United States Patent [19]

Ingolia et al.

[11] Patent Number: 4,960,704

[45] Date of Patent: Oct. 2, 1990

[54] MODIFIED ANTIBIOTIC RESISTANCE GENE

[75] Inventors: Thomas D. Ingolia; Kevin R. Kaster; R. Nagaraja Rao, all of Indianapolis, Ind.

[73] Assignee: Eli Lilly and Company, Indianapolis, Ind.

[21] Appl. No.: 205,011

[22] Filed: May 31, 1988

Related U.S. Application Data

[63] Continuation of Ser. No. 535,508, Sep. 26, 1983, abandoned, which is a continuation-in-part of Ser. No. 533,189, Sep. 19, 1983, abandoned, which is a continuation-in-part of Ser. No. 516,222, Jul. 22, 1983, abandoned.

[51] Int. Cl.$^5$ .................. C12N 1/20; C12N 15/00; C12N 9/12; C07H 15/12
[52] U.S. Cl. .................. 435/252.33; 435/172.3; 435/194; 435/320; 536/27; 935/14; 935/29; 935/69; 935/73
[58] Field of Search .................. 435/68, 172.3, 194, 435/320, 252.33; 536/27; 935/9, 14, 22, 27, 29, 47, 73, 69

[56] References Cited

U.S. PATENT DOCUMENTS 4,468,464  8/1984  Cohen et al. .................. 435/317

FOREIGN PATENT DOCUMENTS 0068740  1/1983  European Pat. Off. ......... 435/172.3
2100738  1/1983  United Kingdom ............. 435/172.3

OTHER PUBLICATIONS

Stewart et al, 1978, "Phosphoglycerate Kinase B from Ram Testis, Purification, Characterization and Comparison with the Muscle Enzyme", *Eur. J. Biochem.*, 85(1), 89-95 (Chem. Abstracts, vol. 88, 185119d).

Kaster et al, 1983, "Analysis of a Bacterial Hygromycin B Resistance Gene by Transcriptional and Translational Fusions and by DNA Seq." *Nuc. Acids Res.*, vol. 11, No. 19, pp. 6895-6911.

Casadaban et al., 1980, "In Vitro Gene Fusions That Join an Enzymatically Active β-Galactosidase Segment to Amino-Terminal Fragments of Exagenous Proteins . . . " *J. Bact.*, vol. 143, pp. 971-980.

Finkelstein et al., 1983, "Heat Shock-Regulated Production of *E. coli* β-Galactosidase in *S. cerevisiae*" *Mol. Cell. Biol.*, vol. 3, pp. 1625-1633.

Davies et al., 1978, "Enzyme Modification of Aminoglycoside Antibiotics: 3-N-Acetyltransferase with Broad Specificity . . . " *Antimicrob. Agents Chemother.*, vol. 14(1), 69-72, in: *Chem. Abstracts*, vol. 89, Abstr. No. 159954y.

Guillemin et al., *Science*, 218:585-587, 1982.
Tabin et al., *Nature*, 300:143-149, 1982.
Reddy et al., *Nature*, 300:149-152, 1982.
Capon et al., *Nature*, 302:33-37, 1983, Mar.
Wilson et al., *The New England Journal of Medicine*, 309(15):900-908, 1983, Oct.
Wilson et al., *Proc. National Acad. Sci.* (USA), 80:870-873, 1983, Feb.

*Primary Examiner*—Thomas D. Mays
*Attorney, Agent, or Firm*—Gerald V. Dahling; Leroy Whitaker

[57] ABSTRACT

A modified hygromycin B resistance-conferring gene either alone or in translational reading phase with a gene or portion of a gene is disclosed. The invention further comprises recombinant DNA cloning vectors and transformants of the aforementioned DNA.

56 Claims, 9 Drawing Sheets

Restriction Site Map of Plasmids pIT123 and pKC222 pIT123 pKC222

Restriction Site Map of Plasmids pKC203 and pIT144 pKC203 pIT144

Restriction Site Map of Plasmids pIT208 and pIT207 pIT208 pIT207

Restriction Site Map of Plasmids pKC307 and pIT125 pKC307 pIT125

Thymosin Alpha I Gene

Synthesis Procedure for Fragment T15

Construction Route for Plasmid pThα1**

Restriction Site Map of Plasmids
pIT215 and pIT217** pIT215 pIT217

Restriction Site Map of Plasmid pIT219 pIT219

MODIFIED ANTIBIOTIC RESISTANCE GENE

CROSS REFERENCE

This application is a continuation of application Ser. No. 06/535,508 filed Sept. 26, 1983, now abandoned, which is a continuation-in-part of application, Ser. No. 533,189, now abandoned filed Sept. 19, 1983, which is a continuation-in-part of Ser. No. 516,222, filed July 22, 1983, now abandoned.

SUMMARY OF THE INVENTION

The present invention is a modified hygromycin B resistance-conferring gene. The modified gene is useful for cloning, isolating and characterizing promoters and also for constructing gene fusions that act as dominant selectable markers in appropriate host cells. The invention further comprises vectors and transformants comprising the aforementioned DNA.

The present invention is related generally to U.S. patent application Ser. No. 487,787, abandoned filed on Apr. 22, 1983. The aforementioned application discloses starting materials, including plasmid pKC222 and the hygromycin B resistance-conferring DNA segment therein, which are useful for constructing the present invention. The application does not, however, disclose the present modified gene or suggest its utility as a critical component of selectable gene-fusions.

Gene fusion with a dominant, selectable marker is a useful way to isolate transcriptional or translational activator sequences and thus to express the dominant selectable marker in a foreign system. Since a wide variety of organisms are sensitive to the aminoglycoside antibiotic hygromycin B (Ahmad et al., 1980, Antimicrob. Agents Chemother. 18:789; Mann et al., 1953, Antibiot. and Chemother. 3:1279; Pettinger et al., 1953, Antibiot. and Chemother. 3:1268; and Singh et al., 1979, Nature 277:146), the modified hygromycin B resistance-conferring gene is a valuable dominant selectable marker for use in diverse host systems.

For purposes of the present invention, the last 338, 339 or 340 amino acids of hygromycin B phosphotransferase refers to a polypeptide comprising, in natural sequence, all the amino acids of hygromycin B phosphotransferase except, with reference to the N-terminus of the naturally occurring hygromycin B phosphotransferase molecule, the first, the first and second, or the first, second and third amino acids. In addition, the following terms are as defined below.

Recombinant DNA Cloning Vector - any autonomously replicating agent, including but not limited to plasmids, comprising a DNA molecule to which one or more additional DNA segments can or have been added.

Transformation - the introduction of DNA into a recipient host cell that changes the genotype and results in a change in the recipient cell.

Transformant - a recipient host cell that has undergone transformation.

Restriction Fragment - any linear portion or whole of plasmid or other DNA generated by the action of one or more restriction enzymes.

Hygromycin B Resistance Genotype - aph(4)
Kanamycin Resistance Genotype - $Km^R$
Ampicillin Resistance Genotype - $Ap^R$
Uracil Prototrophy Genotype - URA 3
Base Pairs - bp Functional Polypeptide - a recoverable bioactive entirely heterologous polypeptide or precursor, a recoverable bioactive polypeptide comprising a heterologous polypeptide and a portion or whole of a homologous polypeptide, or a recoverable bioinactive fusion polypeptide comprising a heterologous polypeptide and a bio-inactivating homologous polypeptide which can be specifically cleaved.

Fused Gene Product - a recoverable heterologous polypeptide which is fused with a portion or whole of a homologous polypeptide.

Structural Gene - DNA that encodes a functional polypeptide but that lacks transcriptional and translational activator sequences.

DETAILED DESCRIPTION OF THE INVENTION

Figure 1:
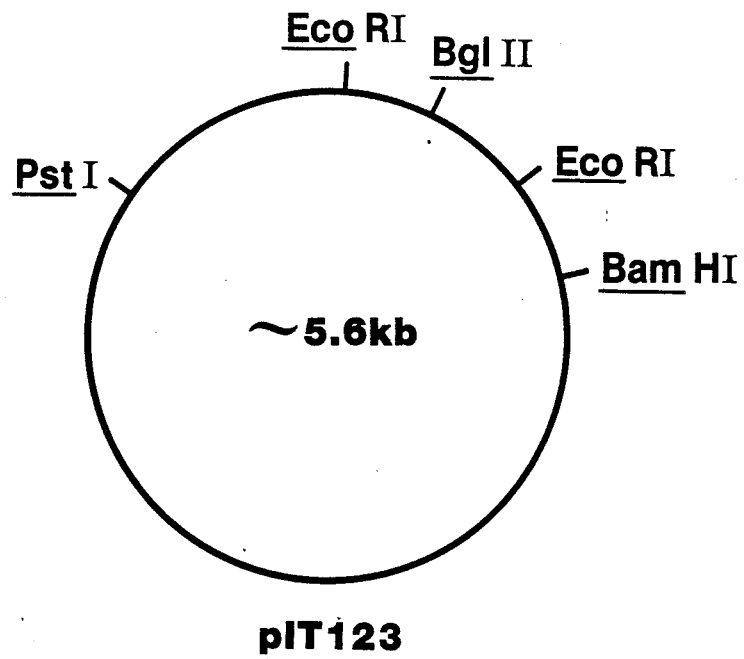
FIG. 1, depicts the restriction site maps of plasmids pIT123 and pKC222.
Figure 1:
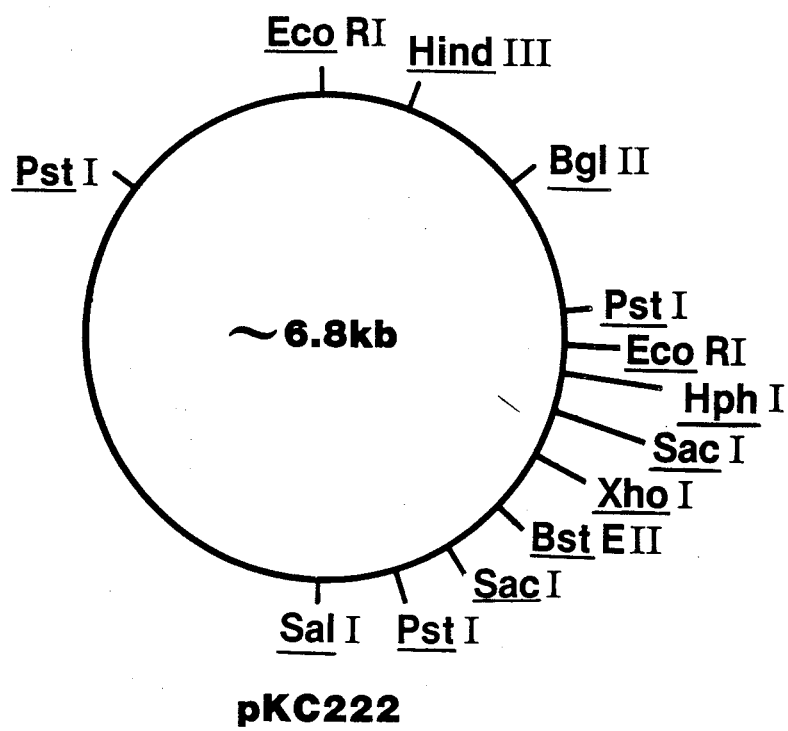

The present invention comprises novel DNA encoding the last 338, 339 or 340 amino acids of hygromycin B phosphotransferase, either alone or in translational reading phase with a transcriptional and translational activator sequence-containing gene or portion of a gene. The invention further comprises recombinant DNA cloning vectors and transformants comprising the aforementioned DNA.

More particularly, the DNA of the present invention comprises the deoxyribonucleotide sequence

-continued

```
R²n CCT GAA    CTC ACC GCG    ACG TCT GTC    GAG AAG TTT CTG
|   ||| |||    ||| ||| |||    ||| ||| |||    ||| ||| ||| |||
R³n GGA CTT    GAG TGG CGC    TGC AGA CAG    CTC TTC AAA GAC
    LYS PRO GLU    LEU THR ALA    THR SER VAL    GLU LYS PHE LEU

ATC GAA AAG    TTC GAC AGC    GTC TCC GAC    CTG ATG CAG CTC
||| ||| |||    ||| ||| |||    ||| ||| |||    ||| ||| ||| |||
TAG CTT TTC    AAG CTG TCG    CAG AGG CTG    GAC TAC GTC GAG
ILE GLU LYS    PHE ASP SER    VAL SER ASP    LEU MET GLN LEU

TCG GAG GGC    GAA GAA TCT    CGT GCT TTC    AGC TTC GAT GTA
||| ||| |||    ||| ||| |||    ||| ||| |||    ||| ||| ||| |||
AGC CTC CCG    CTT CTT AGA    GCA CGA AAG    TCG AAG CTA CAT
SER GLU GLY    GLU GLU SER    ARG ALA PHE    SER PHE ASP VAL

GGA GGG CGT    GGA TAT GTC    CTG CGG GTA    AAT AGC TGC GCC
||| ||| |||    ||| ||| |||    ||| ||| |||    ||| ||| ||| |||
CCT CCC GCA    CCT ATA CAG    GAC GCC CAT    TTA TCG ACG CGG
GLY GLY ARG    GLY TYR VAL    LEU ARG VAL    ASN SER CYS ALA

GAT GGT TTC    TAC AAA GAT    CGT TAT GTT    TAT CGG CAC TTT
||| ||| |||    ||| ||| |||    ||| ||| |||    ||| ||| ||| |||
CTA CCA AAG    ATG TTT CTA    GCA ATA CAA    ATA GCC GTG AAA
ASP GLY PHE    TYR LYS ASP    ARG TYR VAL    TYR ARG HIS PHE

GCA TCG GCC    GCG CTC CCG    ATT CCG GAA    GTG CTT GAC ATT
||| ||| |||    ||| ||| |||    ||| ||| |||    ||| ||| ||| |||
CGT AGC CGG    CGC GAG GGC    TAA GGC CTT    CAC GAA CTG TAA
ALA SER ALA    ALA LEU PRO    ILE PRO GLU    VAL LEU ASP ILE

GGG GAA TTC    AGC GAG AGC    CTG ACC TAT    TGC ATC TCC CGC
||| ||| |||    ||| ||| |||    ||| ||| |||    ||| ||| ||| |||
CCC CTT AAG    TCG CTC TCG    GAC TGG ATA    ACG TAG AGG GCG
GLY GLU PHE    SER GLU SER    LEU THR TYR    CYS ILE SER ARG

CGT GCA CAG    GGT GTC ACG    TTG CAA GAC    CTG CCT GAA ACC
||| ||| |||    ||| ||| |||    ||| ||| |||    ||| ||| ||| |||
GCA CGT GTC    CCA CAG TGC    AAC GTT CTG    GAC GGA CTT TGG
ARG ALA GLN    GLY VAL THR    LEU GLN ASP    LEU PRO GLU THR

GAA CTG CCC    GCT GTT CTG    CAG CCG GTC    GCG GAG GCC ATG
||| ||| |||    ||| ||| |||    ||| ||| |||    ||| ||| ||| |||
CTT GAC GGG    CGA CAA GAC    GTC GGC CAG    CGC CTC CGG TAC
GLU LEU PRO    ALA VAL LEU    GLN PRO VAL    ALA GLU ALA MET

GAT GCG ATC    GCT GCG GCC    GAT CTT AGC    CAG ACG AGC GGG
||| ||| |||    ||| ||| |||    ||| ||| |||    ||| ||| ||| |||
CTA CGC TAG    CGA CGC CGG    CTA GAA TCG    GTC TGC TCG CCC
ASP ALA ILE    ALA ALA ALA    ASP LEU SER    GLN THR SER GLY

TTC GGC CCA    TTC GGA CCG    CAA GGA ATC    GGT CAA TAC ACT
||| ||| |||    ||| ||| |||    ||| ||| |||    ||| ||| ||| |||
AAG CCG GGT    AAG CCT GGC    GTT CCT TAG    CCA GTT ATG TGA
PHE GLY PRO    PHE GLY PRO    GLN GLY ILE    GLY GLN TYR THR

ACA TGG CGT    GAT TTC ATA    TGC GCG ATT    GCT GAT CCC CAT
||| ||| |||    ||| ||| |||    ||| ||| |||    ||| ||| ||| |||
TGT ACC GCA    CTA AAG TAT    ACG CGC TAA    CGA CTA GGG GTA
THR TRP ARG    ASP PHE ILE    CYS ALA ILE    ALA ASP PRO HIS

GTG TAT CAC    TGG CAA ACT    GTG ATG GAC    GAC ACC GTC AGT
||| ||| |||    ||| ||| |||    ||| ||| |||    ||| ||| ||| |||
CAC ATA GTG    ACC GTT TGA    CAC TAC CTG    CTG TGG CAG TCA
VAL TYR HIS    TRP GLN THR    VAL MET ASP    ASP THR VAL SER

GCG TCC GTC    GCG CAG GCT    CTC GAT GAG    CTG ATG CTT TGG
||| ||| |||    ||| ||| |||    ||| ||| |||    ||| ||| ||| |||
CGC AGG CAG    CGC GTC CGA    GAG CTA CTC    GAC TAC GAA ACC
ALA SER VAL    ALA GLN ALA    LEU ASP GLU    LEU MET LEU TRP
```

```
GCC GAG GAC    TGC CCC GAA    GTC CGG CAC    CTC GTG CAC GCG
||| ||| |||    ||| ||| |||    ||| ||| |||    ||| ||| ||| |||
CGG CTC CTG    ACG GGG CTT    CAG GCC GTG    GAG CAC GTG CGC
ALA GLU ASP    CYS PRO GLU    VAL ARG HIS    LEU VAL HIS ALA

GAT TTC GGC    TCC AAC AAT    GTC CTG ACG    GAC AAT GGC CGC
||| ||| |||    ||| ||| |||    ||| ||| |||    ||| ||| ||| |||
CTA AAG CCG    AGG TTG TTA    CAG GAC TGC    CTG TTA CCG GCG
ASP PHE GLY    SER ASN ASN    VAL LEU THR    ASP ASN GLY ARG

ATA ACA GCG    GTC ATT GAC    TGG AGC GAG    GCG ATG TTC GGG
||| ||| |||    ||| ||| |||    ||| ||| |||    ||| ||| ||| |||
TAT TGT CGC    CAG TAA CTG    ACC TCG CTC    CGC TAC AAG CCC
ILE THR ALA    VAL ILE ASP    TRP SER GLU    ALA MET PHE GLY

GAT TCC CAA    TAC GAG GTC    GCC AAC ATC    TTC TTC TGG AGG
||| ||| |||    ||| ||| |||    ||| ||| |||    ||| ||| ||| |||
CTA AGG GTT    ATG CTC CAG    CGG TTG TAG    AAG AAG ACC TCC
ASP SER GLN    TYR GLU VAL    ALA ASN ILE    PHE PHE TRP ARG

CCG TGG TTG    GCT TGT ATG    GAG CAG CAG    ACG CGC TAC TTC
||| ||| |||    ||| ||| |||    ||| ||| |||    ||| ||| ||| |||
GGC ACC AAC    CGA ACA TAC    CTC GTC GTC    TGC GCG ATG AAG
PRO TRP LEU    ALA CYS MET    GLU GLN GLN    THR ARG TYR PHE

GAG CGG AGG    CAT CCG GAG    CTT GCA GGA    TCG CCG CGG CTC
||| ||| |||    ||| ||| |||    ||| ||| |||    ||| ||| ||| |||
CTC GCC TCC    GTA GGC CTC    GAA CGT CCT    AGC GGC GCC GAG
GLU ARG ARG    HIS PRO GLU    LEU ALA GLY    SER PRO ARG LEU

CGG GCG TAT    ATG CTC CGC    ATT GGT CTT    GAC CAA CTC TAT
||| ||| |||    ||| ||| |||    ||| ||| |||    ||| ||| ||| |||
GCC CGC ATA    TAC GAG GCG    TAA CCA GAA    CTG GTT GAG ATA
ARG ALA TYR    MET LEU ARG    ILE GLY LEU    ASP GLN LEU TYR

CAG AGC TTG    GTT GAC GGC    AAT TTC GAT    GAT GCA GCT TGG
||| ||| |||    ||| ||| |||    ||| ||| |||    ||| ||| ||| |||
GTC TCG AAC    CAA CTG CCG    TTA AAG CTA    CTA CGT CGA ACC
GLN SER LEU    VAL ASP GLY    ASN PHE ASP    ASP ALA ALA TRP

GCG CAG GGT    CGA TGC GAC    GCA ATC GTC    CGA TCC GGA GCC
||| ||| |||    ||| ||| |||    ||| ||| |||    ||| ||| ||| |||
CGC GTC CCA    GCT ACG CTG    CGT TAG CAG    GCT AGG CCT CGG
ALA GLN GLY    ARG CYS ASP    ALA ILE VAL    ARG SER GLY ALA

GGG ACT GTC    GGG CGT ACA    CAA ATC GCC    CGC AGA AGC GCG
||| ||| |||    ||| ||| |||    ||| ||| |||    ||| ||| ||| |||
CCC TGA CAG    CCC GCA TGT    GTT TAG CGG    GCG TCT TCG CGC
GLY THR VAL    GLY ARG THR    GLN ILE ALA    ARG ARG SER ALA

GCC GTC TGG    ACC GAT GGC    TGT GTA GAA    GTA CTC GCC GAT
||| ||| |||    ||| ||| |||    ||| ||| |||    ||| ||| ||| |||
CGG CAG ACC    TGG CTA CCG    ACA CAT CTT    CAT GAG CGG CTA
ALA VAL TRP    THR ASP GLY    CYS VAL GLU    VAL LEU ALA ASP

AGT GGA AAC    CGA CGC CCC    AGC ACT CGT    CCG AGG GCA AAG
||| ||| |||    ||| ||| |||    ||| ||| |||    ||| ||| ||| |||
TCA CCT TTG    GCT GCG GGG    TCG TGA GCA    GGC TCC CGT TTC
SER GLY ASN    ARG ARG PRO    SER THR ARG    PRO ARG ALA LYS

GAA R⁴
||| |
CTT R⁵
GLU
``` wherein
- A is deoxyadenyl,
- G is deoxyguanidyl,
- C is deoxycytidyl,
- T is thymidyl,
- R and R² are deoxyribonucleotide triplets that independently encode lysine, R¹ and R³ are deoxyribonucleotide triplets wherein the nitrogenous bases are complementary to the respective and corresponding bases of R and R², m and n=0 or 1, subject to the limitation that when n=0, then m=0 and when m=1, then n=1, and when n=1, m can be 0 or 1, R⁴ is a deoxyribonucleotide triplet that encodes a translational stop codon and R⁵ is a deoxyribonucleotide triplet wherein the nitrogenous bases are complementary to the corresponding bases of R⁴.

The amino acids encoded by the above DNA are designated below the appropriate nucleotide triplet. Accordingly, MET is methionine,
LYS is lysine,
PRO is proline,
GLU is glutamic acid,
LEU is leucine,
THR is threonine,
ALA is alanine,
SER is serine,
VAL is valine,
PHE is phenylalanine,
ILE is isoleucine,
GLY is glycine,
ASP is aspartic acid,
GLN is glutamine,
ARG is arginine,
CYS is cysteine,
TRP is tryptophan,
ASN is asparagine,
HIS is histidine and
TYR is tyrosine.

The present invention, of which R, R¹, R², R³, R⁴ and R⁵ are defined in accordance with the genetic code (Watson, J. D., 1976, Molecular Biology of the Gene, W. A. Benjamin Inc., Menlo Park, Calif.), can be conventionally synthesized by the modified phosphotriester method using fully protected trideoxyribonucleotide building blocks. Such synthetic methods are well known in the art and can be carried out in substantial accordance with the procedure of Itakura et al., 1977, Science 198:1056 and Crea et al., 1978, Proc. Nat. Acad. Sci. USA 75:5765. Those skilled in the art will recognize that other DNA sequences encoding the same amino acids as those encoded by the above illustrative DNA sequence can also be synthesized. These other DNA sequences reflect the degeneracy of the genetic code and thus are within the scope of the present invention.

The above-defined DNA wherein m=O R⁴ is TAG and R⁵ is ATC can also be constructed by appropriate digestion of plasmid pKC222. The convenient HphI restriction site near the beginning of the coding region of the hygromycin B phosphotransferase gene in pKC222 is very useful for this purpose. Thus, HphI-PstI digestion of plasmid pKC222 results in a truncated hygromycin B phosphotransferase gene which comprises 325 bp (plus single stranded extensions) and which encodes amino acids 4-112 of the hygromycin B phosphotransferase polypeptide. After removal of the 3' extension left by the HphI restriction enzyme, the fragment can be provided with a BamHI molecular linker, digested with EcoRI restriction enzyme and then ligated to BamHI-EcoRI-digested plasmid pBR322. The resultant plasmid, designated as pIT122, contains only part of the hygromycin B phosphotransferase gene and is used as a starting material.

Coding information for hygromycin B phosphotransferase amino acids 113-341 can be provided by ligating the ~1.45 kb EcoRI fragment of plasmid pKC222 into appropriately cleaved plasmid pIT122. The resulant plasmid, designated as pIT123, contains the complete hygromycin B phosphotransferase structural gene except for the substitution of the BamHI linker for the first 9 nucleotide pairs. The truncated gene thus encodes a hygromycin B phosphotransferase that lacks the first 3 amino acids encoded by the native gene. A restriction site map of plasmid pIT123 is presented in FIG. 1 of the accompanying drawings.

Figure 2:
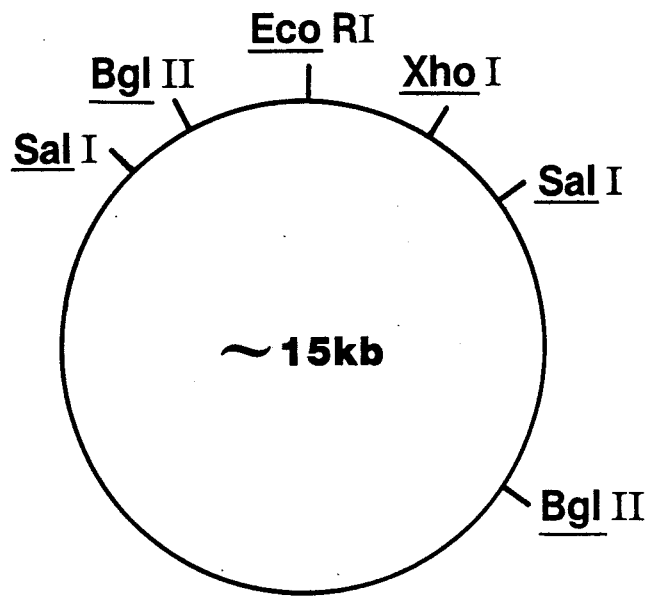
FIG. 2, depicts the restriction site maps of plasmids pKC203 and pIT144.
Figure 2:
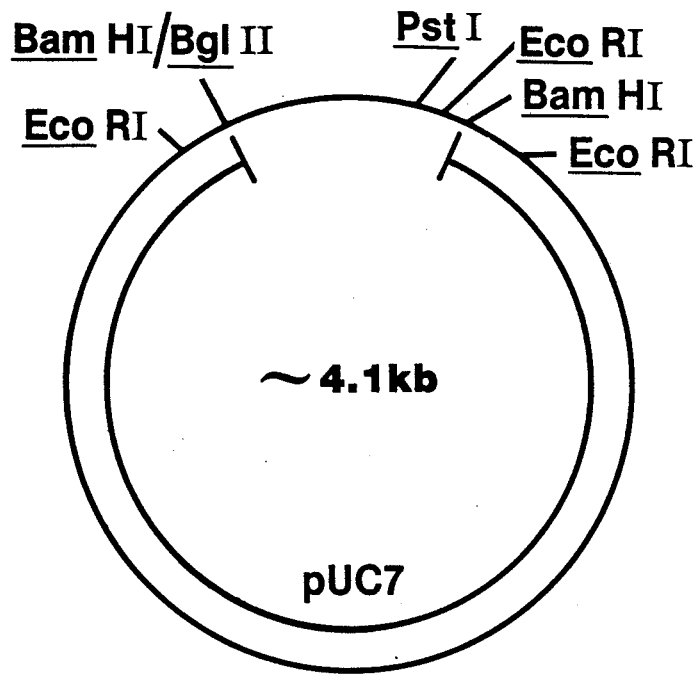

Plasmid pKC222, from which the DNA of the present invention can be obtained, is ~6.8 kb and is constructed by ligating the ~2.75 kb SalI-BglII fragment of plasmid pKC203 to the ~4.1 kb SalI-BglII fragment of plasmid pKC7. Plasmid pKC203 is ~15 kb and can be conventionally isolated from E. coli JR225, a strain deposited and made part of the permanent stock culture collection of the American Type Culture Collection, Rockville, Md. The strain is available to the public as a preferred source and stock reservoir of plasmid pKC203 under the accession number ATCC 31912. Plasmid pKC7 is known in the art (ATCC 37084) and can also be constructed in accordance with the procedure disclosed in Rao and Rogers, 1979, Gene 7:79. A restriction site map of each of plasmids pKC222 and pKC203 is presented respectively in FIGS. 1 and 2 of the accompanying drawings.

The DNA of the present invention is useful as a dominant selectable marker when fused in translational reading phase with a transcriptional and translational activator sequence-containing gene or portion of a gene. The number of amino acids encoded by the gene or portion of a gene is not critical for purposes of the present invention. In the case of a bacterial gene, such a fusion can be made by ligating the truncated aph(4) gene of plasmid pIT123 into plasmid pUC7. Plasmid pUC7, commercially available and constructed in substantial accordance with the teaching of Vieira and Messing, 1982, Gene 9:259, contains a portion of the E. coli lac Z gene and also a unique BamHI restriction site downstream from the lac operator and translation initiation signals. The reading frame at the BamHI site within the lac Z gene fragment is the same as that required for the truncated aph(4) gene of plasmid pIT123. Accordingly, joining the two genes at the BamHI site by ligating the ~1.3 kb BamHI-BglII fragment of plasmid pIT123 into BamHI digested plasmid pUC7 results in a hybrid gene that is capable of conferring resistance to hygromycin B. Such illustrative construction comprises the coding sequence for the first twelve amino acids of lac Z fused with truncated aph(4)gene. A restriction site map of the resultant gene-containing plasmid, designated as pIT144, is presented in FIG. 2 of the accompanying drawings. A similar plasmid, designated as pKC307, was constructed by ligating blunt ended HphI-digested plasmid pIT104 into blunt ended HincII-digested plasmid pUC8. The latter plasmid is similar to plasmid pUC7 and is also commercially available and constructed in substantial accordance with the teaching of Vieira and Messing, 1982.

The DNA of the present invention can also be fused with eukaryotic genes or portions of genes, such as, for example, the yeast heat shock cognate gene (YG101), disclosed in Ingolia et al., 1982, Mol. and Cellular Biol.

Figure 3:
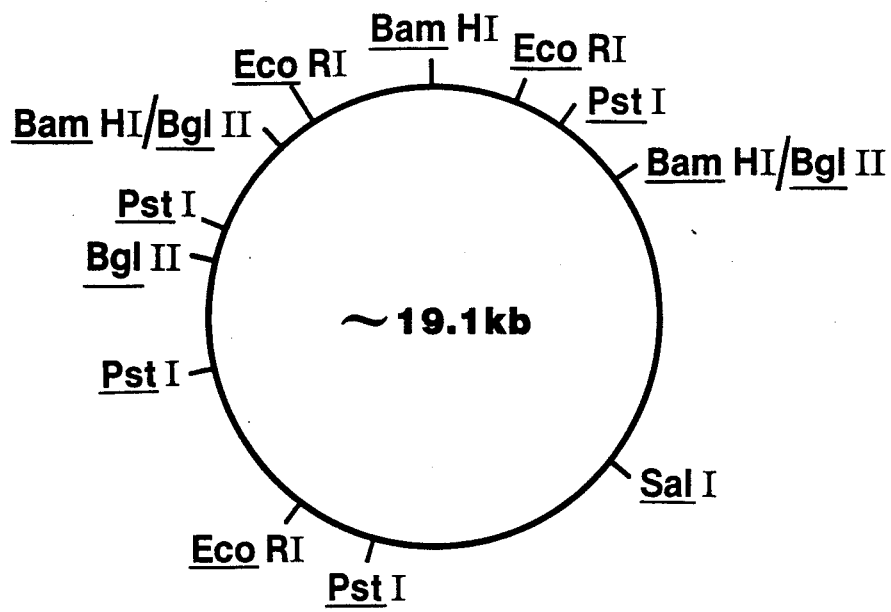
FIG. 3, depicts the restriction site maps of plasmids pIT208 and pIT207.
Figure 3:
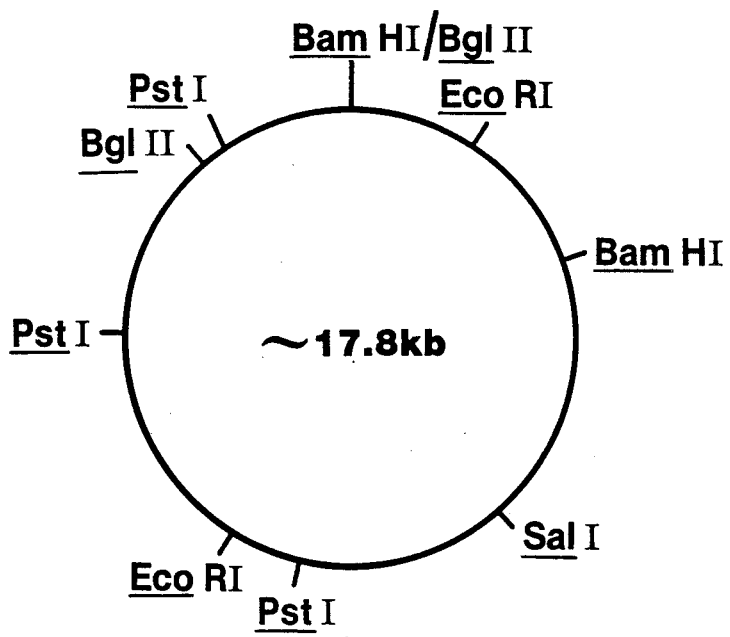

2:1388. The ability to mobilize the transcriptional and translational activator sequences of YG101 on a 750 bp BamHI-B91II fragment of plasmid pIT118 allows for an especially convenient fusion. This is done by first constructing plasmid pIT207, an intermediate plasmid comprising the aforementioned transcriptional and translational activator sequence-containing fragment ligated into BamHI restricted plasmid pMC1587. Ligation of the ~1.3 kb BamHI-BglII fragment of plasmid pIT123 into BamHI-digested plasmid pIT207 results in the bifunctional plasmid pIT208. Plasmid pIT208 is selectable in *E. coli*, confers resistance to antibiotic hygromycin B in yeast and thus is illustrative of the present invention. A restriction site map of plasmid pIT208 is presented in FIG. 3 of the accompanying drawings.

The heat shock gene (YG100), also disclosed in Ingolia et al., 1982, can similarly be used for constructing convenient translational fusions. This is done by ligating the transcriptional and translational activator sequence-containing ~1 kb BamHI-BglII fragment of plasmid pIT120 into BamHI-digested plasmid pIT213. The latter plasmid comprises the known plasmid pRB5, a kanamycin resistance gene and the aforementioned truncated hygromycin B resistance gene-containing ~1.3 kb BamHI-BglII fragment of plasmid pIT123. Plasmid pIT120, from which the hs100 transcriptional and translational activator sequence can be obtained, can be conventionally isolated from *coli* K12 JA221/pIT120, a strain deposited and made part of the permanent stock culture collection of the Northern Regional Research Laboratory, Peoria, Ill. The strain is available to the public as a preferred source and stock reservoir of the plasmid under the accession number NRRL B-15603. The aforementioned ligation of the pIT120 and pIT213 fragments results in the illustrative bifunctional plasmid pIT217. Plasmid pIT217 is selectable in E. coli, confers resistance to hygromycin B in yeast and thus further exemplifies the present invention.

Those skilled in the art will recognize that ligation of the aforementioned BamHI-digested plasmid pIT213 and the 750 bp BamHI-BglII fragment of plasmid pIT118 results in an illustrative fusion which is also within the scope of the present invention. The resultant plasmid, designated as pIT215, is selectable in *E. coli and confers hygromycin B resistance in yeast. Additional constructions employing different genes can also be made. For example, the eukaryotic phosphoglycerate kinase gene (PGK) can be fused with the present truncated hygromycin B resistance-conferring DNA by ligating the transcriptional and translational activater sequence-containing 230 bp BamHI fragment of plasmid pIT143 into BamHI-digested plasmid pIT213. Plasmid pIT143, from which the PGK transcriptional and translational activator sequence is obtained, is constructed by digesting the 958 bp ClaI-HincII fragment of plasmid pIT141 with the restriction enzyme MboII, removing the resultant extensions with the Klenow fragment of DNA polymerase, attaching BamHI linkers with the sequence TGGATCCA and then ligating the linker-containing fragment into BamHI-digested plasmid pUC8. Plasmid pIT141, which contains the entire PGK gene, is used to construct plasmid pIT143 and can be conventionally isolated from E. coli* K12 JA221/pIT141, a strain deposited and made part of the permanent stock culture collection of the Northern Regional Research Laboratory, Peoria, Ill. The strain is available to the public as a preferred source and stock reservoir of the plasmid under the accession number NRRL B-15602.

Those skilled in the art will recognize that a wide variety of genes or portions of genes can be substituted for the illustrative bacterial lac Z and eukaryotic PGK, YG100 and YG101 genes exemplified above. The number of amino acids encoded by such genes or portions of genes is not critical for purposes of the present invention. Other genes include genes from (1) *E. coli*, such as, for example, the trpE and lipoprotein genes; (2) *Saccharomyces cerevisiae*, such as for example, the alpha factor gene; (3) *Bacillus*, such as, for example, the alpha amylase and spoVG genes; (4) *Streptomyces* such as, for example, the thiostrepton resistance, neomycin resistance and viomycin resistance genes; (5) viruses or bacteriophages, such as, for example, the genes transcribed by $\lambda_{PL}$ and $\lambda_{PR}$ promoters; (6) mammals, such as, for example, the thymidine kinase and dihydrofolate reductase genes; and (7) plants, such as, for example, the octopine synthetase and nopaline synthetase genes.

The aforementioned genes can be truncated by treatment with an appropriate restriction enzyme and/or Bal31 nuclease and then, depending upon convenience and the particular fusion desired, provided with molecular linkers. Molecular linkers are commercially available or, if a special or unusual gene fusion is desired, constructed in accordance with the teaching of Itakura et al., 1977 and Crea et al. 1978. A particularly useful fusion results from ligating the ~1.3 kb truncated aph(4) gene-containing fragment of plasmid pIT123 into the ~4.5 kb BamHI-BglII fragment of plasmid pIA7Δ4Δ1. The latter fragment contains the transcriptional and translational activator sequence and also a 15 amino acid coding region of the bacterial trp LE' gene. The aforementioned ligation results in the illustrative ~5.8 kb plasmid pIT125. Those skilled in the art will recognize that fusing the other aforementioned truncated genes, with or without molecular linkers, to the present truncated aph(4) gene also results in vectors illustrative and within the scope of the present invention.

Vectors comprising the present DNA can be used in any hygromycin B sensitive host cell provided (1) that the vector replicates in the host cell or is integrated into the host cell chromosome; (2) that the gene fused to the truncated aph(4) gene is expressed in the host cell; and (3) that the host cell is susceptible to transformation. Illustrative and particularly useful host cells include, for example, *E. coli, E. coli* K12, *E coli* K12 JA221, *E. coli* K12 HB101, *E. coli K*12 RR1, Streptomyces, *Streptomyces ambofaciens*, Bacillus, *Bacillus subtilis, Saccharomyces cerevisiae*, mammalian cells and plant cells, especially Angiospermous cells. Those skilled in the art will recognize that other host cells transformed by vectors comprising the present DNA are also illustrative and within the scope of the present invention.

While all the embodiments of the present invention are useful, some of the present DNA sequences, cloning vectors and transformants are preferred. Accordingly, preferred DNA sequences are the ~1.3 kb BamHI-BglII fragment of plasmid pIT123 and the sequence

```
CCT GAA CTC    ACC GCG ACG    TCT GTC GAG AAG
||| ||| |||    ||| ||| |||    ||| ||| ||| |||
GGA CTT GAG    TGG CGC TGC    AGA CAG CTC TTC
```

```
TTT CTG ATC    GAA AAG TTC    GAC AGC GTC    TCC GAC CTG ATG
| | | | | | | | |    | | | | | | | | |    | | | | | | | | |    | | | | | | | | | | | |
AAA GAC TAG    CTT TTC AAG    CTG TCG CAG    AGG CTG GAC TAC

CAG CTC TCG    GAG GGC GAA    GAA TCT CGT    GCT TTC AGC TTC
| | | | | | | | |    | | | | | | | | |    | | | | | | | | |    | | | | | | | | | | | |
GTC GAG AGC    CTC CCG CTT    CTT AGA GCA    CGA AAG TCG AAG

GAT GTA GGA    GGG CGT GGA    TAT GTC CTG    CGG GTA AAT AGC
| | | | | | | | |    | | | | | | | | |    | | | | | | | | |    | | | | | | | | | | | |
CTA CAT CCT    CCC GCA CCT    ATA CAG GAC    GCC CAT TTA TCG

TGC GCC GAT    GGT TTC TAC    AAA GAT CGT    TAT GTT TAT CGG
| | | | | | | | |    | | | | | | | | |    | | | | | | | | |    | | | | | | | | | | | |
ACG CGG CTA    CCA AAG ATG    TTT CTA GCA    ATA CAA ATA GCC

CAC TTT GCA    TCG GCC GCG    CTC CCG ATT    CCG GAA GTG CTT
| | | | | | | | |    | | | | | | | | |    | | | | | | | | |    | | | | | | | | | | | |
GTG AAA CGT    AGC CGG CGC    GAG GGC TAA    GGC CTT CAC GAA

GAC ATT GGG    GAA TTC AGC    GAG AGC CTG    ACC TAT TGC ATC
| | | | | | | | |    | | | | | | | | |    | | | | | | | | |    | | | | | | | | | | | |
CTG TAA CCC    CTT AAG TCG    CTC TCG GAC    TGG ATA ACG TAG

TCC CGC CGT    GCA CAG GGT    GTC ACG TTG    CAA GAC CTG CCT
| | | | | | | | |    | | | | | | | | |    | | | | | | | | |    | | | | | | | | | | | |
AGG GCG GCA    CGT GTC CCA    CAG TGC AAC    GTT CTG GAC GGA

GAA ACC GAA    CTG CCC GCT    GTT CTG CAG    CCG GTC GCG GAG
| | | | | | | | |    | | | | | | | | |    | | | | | | | | |    | | | | | | | | | | | |
CTT TGG CTT    GAC GGG CGA    CAA GAC GTC    GGC CAG CGC CTC

GCC ATG GAT    GCG ATC GCT    GCG GCC GAT    CTT AGC CAG ACG
| | | | | | | | |    | | | | | | | | |    | | | | | | | | |    | | | | | | | | | | | |
CGG TAC CTA    CGC TAG CGA    CGC CGG CTA    GAA TCG GTC TGC

AGC GGG TTC    GGC CCA TTC    GGA CCG CAA    GGA ATC GGT CAA
| | | | | | | | |    | | | | | | | | |    | | | | | | | | |    | | | | | | | | | | | |
TCG CCC AAG    CCG GGT AAG    CCT GGC GTT    CCT TAG CCA GTT

TAC ACT ACA    TGG CGT GAT    TTC ATA TGC    GCG ATT GCT GAT
| | | | | | | | |    | | | | | | | | |    | | | | | | | | |    | | | | | | | | | | | |
ATG TGA TGT    ACC GCA CTA    AAG TAT ACG    CGC TAA CGA CTA

CCC CAT GTG    TAT CAC TGG    CAA ACT GTG    ATG GAC GAC ACC
| | | | | | | | |    | | | | | | | | |    | | | | | | | | |    | | | | | | | | | | | |
GGG GTA CAC    ATA GTG ACC    GTT TGA CAC    TAC CTG CTG TGG

GTC AGT GCG    TCC GTC GCG    CAG GCT CTC    GAT GAG CTG ATG
| | | | | | | | |    | | | | | | | | |    | | | | | | | | |    | | | | | | | | | | | |
CAG TCA CGC    AGG CAG CGC    GTC CGA GAG    CTA CTC GAC TAC

CTT TGG GCC    GAG GAC TGC    CCC GAA GTC    CGG CAC CTC GTG
| | | | | | | | |    | | | | | | | | |    | | | | | | | | |    | | | | | | | | | | | |
GAA ACC CGG    CTC CTG ACG    GGG CTT CAG    GCC GTG GAG CAC

CAC GCG GAT    TTC GGC TCC    AAC AAT GTC    CTG ACG GAC
| | | | | | | | |    | | | | | | | | |    | | | | | | | | |    | | | | | | | | |
GTG CGC CTA    AAG CCG AGG    TTG TTA CAG    GAC TGC CTG

AAT GGC CGC    ATA ACA GCG    GTC ATT GAC    TGG AGC GAG GCG
| | | | | | | | |    | | | | | | | | |    | | | | | | | | |    | | | | | | | | | | | |
TTA CCG GCG    TAT TGT CGC    CAG TAA CTG    ACC TCG CTC CGC
```

```
ATG TTC GGG    GAT TCC CAA    TAC GAG GTC    GCC AAC ATC TTC
||| ||| |||    ||| ||| |||    ||| ||| |||    ||| ||| ||| |||
TAC AAG CCC    CTA AGG GTT    ATG CTC CAG    CGG TTG TAG AAG

TTC TGG AGG    CCG TGG TTG    GCT TGT ATG    GAG CAG CAG ACG
||| ||| |||    ||| ||| |||    ||| ||| |||    ||| ||| ||| |||
AAG ACC TCC    CGC ACC AAC    CGA ACA TAC    CTC GTC GTC TGC

CGC TAC TTC    GAG CGG AGG    CAT CCG GAG    CTT GCA GGA TCG
||| ||| |||    ||| ||| |||    ||| ||| |||    ||| ||| ||| |||
GCG ATG AAG    CTC GCC TCC    GTA GGC CTC    GAA CGT CCT AGC

CCG CGG CTC    CGG GCG TAT    ATG CTC CGC    ATT GGT CTT GAC
||| ||| |||    ||| ||| |||    ||| ||| |||    ||| ||| ||| |||
GGC GCC GAG    GCC CGC ATA    TAC GAG GCG    TAA CCA GAA CTG

CAA CTC TAT    CAG AGC TTG    GTT GAC GGC    AAT TTC GAT GAT
||| ||| |||    ||| ||| |||    ||| ||| |||    ||| ||| ||| |||
GTT GAG ATA    GTC TCG AAC    CAA CTG CCG    TTA AAG CTA CTA

GCA GCT TGG    GCG CAG GGT    CGA TGC GAC    GCA ATC GTC CGA
||| ||| |||    ||| ||| |||    ||| ||| |||    ||| ||| |||·|||
CGT CGA ACC    CGC GTC CCA    GCT ACG CTG    CGT TAG CAG GCT

TCC GGA GCC    GGG ACT GTC    GGG CGT ACA    CAA ATC GCC CGC
||| ||| |||    ||| ||| |||    ||| ||| |||    ||| ||| ||| |||
AGG CCT CGG    CCC TGA CAG    CCC GCA TGT    GTT TAG CGG GCG

AGA AGC GCG    GCC GTC TGG    ACC GAT GGC    TGT GTA GAA GTA
||| ||| |||    ||| ||| |||    ||| ||| |||    ||| ||| ||| |||
TCT TCG CGC    CGG CAG ACC    TGG CTA CCG    ACA CAT CTT CAT

CTC GCC GAT    AGT GGA AAC    CGA CGC CCC    AGC ACT CGT CCG
||| ||| |||    ||| ||| |||    ||| ||| |||    ||| ||| ||| |||
GAG CGG CTA    TCA CCT TTG    GCT GCG GGG    TCG TGA GCA GGC

AGG GCA AAG    GAA TAG
||| ||| |||    ||| |||
TCC CGT TTC    CTT ATC
``` wherein
  A is deoxyadenyl,
  G is deoxyguanidyl,
  C is deoxycytidyl and
  T is thymidyl;
preferred plasmids are plasmids pIT123, pIT125, pKC307, pIT208, pIT215, pIT217, pIT219 and pIT44; and preferred transformants are *E. coli* K12 JA221/pIT23, *E. coli* K12 JA221/pIT125, *E. coli* 12 JA221/pKC307, *E. coli* K12 JA221/pIT208, *E. coli* K12 JA221/pIT215, *E. coli* K12 JA221/pIT217, *E. coli* K12 JA221/pIT219, *E. coli* K12 JA221/pIT144 and *Saccharomyces cerevisiae*/pIT208, *Saccharomyces cerevisiae*/pIT215, *Saccharomyces cerevisiae*/pIT217 and *Saccharomyces cerevisiae*/pIT219.

The DNA of the present invention is useful as a selectable marker in both homologous (*E. coli*) and heterologous (non-*E. coli*) systems and thus allows for the construction of selectable vehicles for cloning genes into host cells of diverse nature. The ability of the present DNA to confer resistance to antibiotic hygromycin B also provides a functional test for selecting transformants. This is important because of the practical necessity for determining and selecting the particular cells that have acquired the vector DNA. Additional DNA segments, that lack functional tests for their presence, can be inserted into the vectors and then transformants containing the non-selectable DNA can be isolated by antibiotic hygromycin B selection. Such non-selectable DNA segments include, but are not limited to, genes that specify human insulin A chain, human insulin B chain, human proinsulin, human preproinsulin, human growth hormone, bovine growth hormone, porcine growth hormone, avian growth hormone, human interferon and non-human interferon.

More particularly, a non-selectable DNA segment that comprises a gene is inserted on a plasmid, such as, for example, illustrative plasmid pIT144 or PIT208. The non-selectable DNA can be inserted into one of the EcoRI sites of pIT144 after a partial digestion of pIT144 with SalI or into the SmaI site of pIT208. The desired recombinant is identified by colony hybridization of cells transformed with the litigation mixture using a nick translated probe. After confirming the presence of the non-selectable DNA, the vectors are further amplified in *E. coli* and then, in the case of plasmid pIT208, introduced into yeast. Yeast transformants are readily identified by antibiotic hygromycin B selection. Therefore, the ability to select for antibiotic resistance allows for the efficient isolation of the extremely rare cells that contain the particular non-selectable DNA of interest.

The functional test for hygromycin B resistance, as described herein above, is also used to identify DNA segments that can act as control elements for directing gene expression. Such segments, including but not limited to, promoters, attenuators, repressors, inducers, ribosomal binding sites, and the like, are used to control the expression of economically important genes. In addition, the present invention is useful for isolating and identifying origins of replication. This is done by cloning DNA fragments into vectors that contain the present aph(4) gene fusion and then transforming appropriate host cells under conditions of hygromycin B selection. Hygromycin B resistant cells can then be selected and the DNA used to transform E. coli, thus facilitating isolation of replicons from practically any organism of interest.

The resistance-conferring vectors of the present invention are also useful for insuring that linked DNA fragments are stably maintained in E. coli, yeast and other transformants. These genes or DNA fragments, covalently linked to the present aph(4) gene fusion, are maintained by exposing the transformants to levels of hygromycin B that are toxic to non-transformed cells. Therefore, transformants that lose the vector, and consequently any covalently linked DNA, cannot grow and are eliminated from the culture. This is particularly important in large scale fermentation where the maximum efficiency of product expression is desired.

The present DNA, cloning vectors and transformants are particularly useful for cloning genes which directly or indirectly encode specific functional polypeptides or fused gene products such as, for example, human insulin A chain, human insulin B chain, human proinsulin, human preproinsulin, human growth hormone, non-human growth hormone, human and non-human interferon, and the like; enzymatic functions in metabolic pathways leading to commercially important processes and compounds; control elements that improve gene expression or vector replication; or any physiologically active enzyme of research or commercial value. DNA sequences encoding enzymatic functions include, but are not limited to, sequences that code for enzymes that catalyze synthesis of cephalosporin antibiotics, actaplanin, penicillin, penicillin derivatives and tylosin. Those skilled in the art will understand that the present invention is broadly applicable and thus not limited to the cloning of the particular genes specified above.

The following examples further illustrate and detail the invention disclosed herein. Both an explanation of and the actual procedures for constructing the invention are described where appropriate.

EXAMPLE 1

Construction of Plasmid pKC222 Starting Material

A. Isolation of Plasmid pKC203 and Construction of E. coli K12 BE827/pKC203

The bacterium E. coli JR225 (ATCC No. 31912) was cultured in TY broth (1% tryptone, 0.5% yeast extract, 0.5% sodium chloride, pH 7.4) with 100 µg./ml. of antibiotic hygromycin B according to conventional microbiological procedures. After 18 hours incubation, about 0.5 ml. of the culture was transferred to a 1.5 ml. Eppendorf tube and centrifuged for about 15 seconds. Unless otherwise indicated, all the manipulations were done at ambient temperature. The resultant supernatant was carefully removed with a fine-tip aspirator and the cell pellet was suspended in about 100 µl of freshly prepared lysozyme solution which contained 2 mg./ml. lysozyme, 50 mM glucose, 10 mM CDTA (cyclohexane diaminetetracetate) and 25 mM Tris-HCl (pH 8.0). After incubation at 0° C. for 30 minutes, about 200 µl of alkaline SDS (sodium dodecyl sulfate) solution (0.2N NaOH, 1% SDS) were added and the tube was gently vortexed and then maintained at 0° C. for 15 minutes. Next, about 150 ml. of 3M sodium acetate (prepared by dissolving 3 moles of sodium acetate in a minimum of water, adjusting the pH to 4.8 with glacial acetic acid, and then adjusting the volume to 1l.) were added and the contents of the tube were then mixed gently by inversion for a few seconds during which time a DNA clot formed.

The tube was maintained at 0° C. for 60 minutes and then centrifuged or 5 minutes to yield an almost clear supernatant. About 0.4 ml. of the supernatant was transferred to a second centrifuge tube to which 1 ml. of cold ethanol was added. After the tube was held at −20° C. for 30 minutes, the resultant precipitate was collected by centrifugation (2 minutes) and the supernatant was removed by aspiration. The thus collected pellet was dissolved in 100 µl. of 0.1M sodium acetate/0.05M Tris-HCl (pH 8) and was reprecipitated by the addition of 2 volumes of cold ethanol. After 10 minutes at 20° C., the desired E. coli JR225 plasmid DNA precipitates was collected by centrifugation as described above.

The E. coli JR225 plasmid DNA pellet was dissolved in about 40 µl. of water or dilute buffer, and then used to transform E. coli K12 BE827 in substantial accordance with the transformation method of Wensink, 1974, Cell 3:315. E. coli K12 BE827 has been deposited and made part of the permanent stock culture collection of the American Type Culture Collection, Rockville, Md., from which it is available to the public under the number ATCC 31911. The resultant transformants were selected on TY agar (1% tryptone, 0.5% yeast extract, 0.5% sodium chloride, 1.5% agar, pH 7.4) containing 200 µg./ml. of antibiotic hygromycin B. Some of the transformants, as shown by gel electrophoresis (Rao and Rogers, 1978, Gene 3:247) and other tests, contained both large and smaller (~15 kb) plasmids and were resistant to both antibiotics ampicillin and hygromycin B. Other transformants contained only the smaller ~15 kb plasmid and were resistant to antibiotics hygromycin B and G418 but were sensitive to ampicillin.

Transformants of the latter type were plated on TY agar containing 0.1 mg./ml. of antibiotic hygromycin B and were cultured using standard microbiological techniques. The resultant cells were used to isolate the above described ~15 kb hygromycin B and G418 resistance-conferring plasmid, hereinafter designated as plasmid pKC203. The presence of the antibiotic hygromycin B and G418 resistance genes on plasmid pKC203 was confirmed by subsequent transformation and selection analysis.

B. Construction of Plasmid pKC222 and Transformant E. coli K12 JA221/pKC222

1. Isolation of the ~2.75 kb SalI/BglII Fragment Plasmid pKC203

About 5 µg. of plasmid pKC203 DNA were treated with SalI and BglII restriction enzymes according to the instructions and under the conditions specified by the manufacturer*. In addition, useful procedures for restriction enzyme digestion are also disclosed in Maniatis et al., 1982, Molecular Cloning, Cold Spring Harbor Laboratory, Cold Spring Harbor, N.Y. An ~2.75 kb fragment that contained the genes and control elements for resistance to antibiotics hygromycin B and G418 was recovered by conventional procedures (Maniatis et al., 1982).

*Unless otherwise indicated, restriction enzymes, T4 DNA ligase, DNA polymerase and Klenow fragment (including instructions for their use) can be obtained from the following source: New England Biolabs, 32 Tozer Road, Beverly, Mass. 1915

2. Ligation and Final Construction

About 5 μg. of plasmid pKC7 (ATCC 37084), which can be constructed in accordance with the teaching of Rao and Rogers, 1979, Gene 7:79, were treated with SalI and BglII restriction enzymes. After the enzymes were inactivated by heating at 70° C. for 5 minutes, about 1 μg. of the DNA was mixed in a 1:1 ratio with the ~2.75 kb SalI/BglII fragment of pKC203. The fragments were joined using T4 DNA ligase according to the instructions and under the conditions specified by the manufacturer as cited in Example 1B-1. In addition, useful procedures for both restriction enzyme digestion and ligation are also disclosed in Maniatis et al., 1982. The resulting plasmid pKC222 was transformed into $E.$ $coli$ K12 JA221 (NRRL B-15211) in substantial accordance with the teaching of Example 1A. The resultant transformants were selected on TY agar (1% tryptone, 0.5% yeast extract, 0.5% NaCl, 1.5% agar) containing 50 μg./ml. of antibiotic ampicillin. Transformants were then screened for the desired plasmid. 3. Isolation of Plasmid pKC222

Purified transformants were cultured in TY broth (1% tryptone, 0.5% yeast extract, 0.5% sodium chloride, pH 7.4) with 50 μg./ml. of antibiotic ampicillin according to conventional microbiological procedures. After 18 hours incubation, about 0.5 ml. of the culture was transferred to a 1.5 ml. Eppendorf tube and centrifuged for about 15 seconds. Unless otherwise indicated, all the manipulations were done at ambient temperature. The resultant supernatant was carefully removed with a fine-tip aspirator and the cell pellet was suspended in about 100 μl of freshly prepared lysozyme solution which contained 2 μg./ml. lysozyme, 50 mM glucose, 10 mM CDTA (cyclohexane diaminetetracetate) and 25 mM Tris-HCl (pH 8). After incubation at 0° C. for 30 minutes, about 200 μl of alkaline SDS (sodium dodecyl sulfate) solution (0.2N NaOH, 1% SDS) were added and the tube was gently vortexed and then maintained at 0° C. for 15 minutes. Next, about 150 μl of 3M sodium acetate (prepared by dissolving 3 moles of sodium acetate in a minimum of water, adjusting the pH to 4.8 with glacial acetic acid and then adjusting the volume to 1 l.) were added and the contents mixed gently for a few seconds by inversion. A DNA clot formed, after which the resultant mixture was maintained at 0° C. for 60 minutes and then centrifuged for 5 minutes to yield an almost clear supernatant. About 0.4 ml. of the supernatant were transferred to a second centrifuge tube to which 1 ml. of cold ethanol was added. After the tube was held at −20° C. for 30 minutes, the resultant precipitate was collected by centrifugation (2 minutes) and the supernatant was removed by aspiration. The thus collected pellet was dissolved in 100 μl of 0.1M sodium acetate/0.05M Tris-HCl (pH 8) and was reprecipitated by the addition of 2 volumes of cold ethanol. After 10 minutes at −20° C., the precipitate was collected, as described above, by centrifugation and constituted the desired pKC222 DNA as determined by agarose gel electrophoresis (Rao and Rogers, 1978).

EXAMPLE 2

Construction of Plasmid pIT123 and $E.$ $coli$ K12 JA221/pIT123

A. Isolation of the HphI-PstI Fragment of Plasmid pKC222

About 50 μg. of plasmid pKC222 DNA were digested in 1X HphI salts (6 mM KCl, 10 mM Tris-HCl, pH 7.4, 10 mM MgCl$_2$, 1 mM dithiothreitol) in a total volume of 100 μl with 20 New England Biolab Units of HphI restriction endonuclease. Completion of digestion was checked by electrophoresing 2% of the reaction mixture on agarose. After the NaCl concentration was adjusted to 60 mM by addition of an appropriate volume of 5M NaCl, about 20 units of PstI restriction endonuclease were added. Completion of digestion was again monitored by agarose gel electrophoresis. The desired 325 bp (plus single stranded extensions) HphI-PstI fragment was purified from acrylamide using standard techniques (Schlief and Wensink, 1981, Practical Methods in Molecular Biology. Springer-Verlag, N.Y.).

The purified 325 bp fragment was treated with $E.$ $coli$ DNA polymerase I large fragment (New England Biolabs). Thus, about 1.5 μl. (1 μg.) of fragment, 0.5 μl. of 10X buffer (0.5M Tris, pH 7.5, 0.1M MgCl$_2$), 0.5 μl. each of (200 mM) dCTP, dATP, TTP and dGTP and 1 μl. (containing 1 unit) of DNA polymerase I large (Klenow) fragment were incubated at 37° C. for 15 minutes. After heat inactivation of the polymerase, BamHI linkers were added in substantial accordance with the procedure of Roberts and Lauer, 1979, Methods in Enzymology 68:473. The resultant BamHI linker-containing DNA was conventionally digested with BamHI restriction enzyme in 1X BamHI salts (0.15M NaCl, 6 mM Tris-HCl, pH 7.9, 6 mM MgCl$_2$). Next, the Tris-HCl concentration was increased to 100 mM with an appropriate volume of 2M Tris-HCl, pH 7.4 and then the DNA was further digested with EcoRI restriction enzyme. The resultant digested DNA was again electrophoresed on a 7% acrylamide gel and the desired 250 bp fragment was purified as before.

B. Construction of Plasmid pIT122 and $E.$ $coli$ K12 JA221/pIT122

About 2 μg. of pBR322 DNA were sequentially digested with BamHI and EcoRI restriction enzymes in substantial accordance with the teaching of Example 2A. After the enzymes were inactivated by heating at 70° C. for 5 minutes, about 1 μl. (1 μg.) of the pBR322 DNA was mixed with about 1 μl. (1 μg.) of the purified 250 bp fragment, 37 μl water, 5 μl. (10 mM) ATP, 5 μl. ligation mix (0.5M Tris-HCl, pH 7.8, 0.1M dithiothreitol, 0.1M MgCl$_2$), and 1 μl. T4 DNA ligase (approximately 100,000 New England Biolabs Units). The mixture was incubated at 15° C. for about 2 hours and then the reaction was terminated by incubation at 70° C. for 5 minutes. After cooling on ice, the resultant ligated mixture was used to transform, in substantial accordance with the transformation procedure of Wensink, 1974, $E.$ $coli$ K12 JA221 (NRRL B-15211) on TY plates containing ampicillin at 200 μg./ml. The identity of the desired transformants was conventionally confirmed by testing for the expected phenotype (Amp$^R$, Tet$^S$) and also for the appropriate EcoRI-BamHI insert. The resultant $E.$ $coli$ K12 JA221/pIT122 transformants were conventionally cultured for subsequent production and isolation of plasmid pIT122.

C. Ligation of ~1.45 kb EcoRI Fragment of Plasmid pKC222 into EcoRI-Digested Plasmid pIT122

About 20 μg. of plasmids pKC222 and pIT122 were independently cleaved in separate reaction volumes of 200 μl. each with 40 units of EcoRI restriction enzyme in 1X EcoRI reaction mix (0.1M Tris-HCl, pH 7.5, 0.05M NaCl, 0.005M MgCl$_2$). The desired ~1.45 kb EcoRI fragment was conventionally purified from a 7% acrylamide gel and ligated into the EcoRI-digested pIT122. The resultant ligated DNA was designated as plasmid pIT123 and was then used to transform *E. coli* K12 JA221 (NRRL B-15211). Both the ligation and transformation procedures were carried out in substantial accordance with the teaching of Example 2B. The ampicillin resistant transformants were conventionally screened for the presence and correct orientation of the ~1.45 kb EcoRI fragment by restriction enzyme and agarose gel electrophoretic analysis of the constitutive plasmids. Plasmids containing the entire aph(4) gene, except for first 9 base pairs, constituted the desired plasmid pIT123. The thus identified *E. coli* K12 JA221/pIT123 transformants were then cultured for subsequent production and isolation of plasmid pIT123. A restriction site map of plasmid pIT123 is presented in FIG. 1 of the accompanying drawings.

EXAMPLE 3

Construction of Plasmid pIT144 and *E. coli* K12 RR1ΔM15/pIT144

A. Construction and Isolation of the ~1.3 kb BamHI-BglII Fragment of Plasmid pIT123

The desired digestion and isolation were carried out in substantial accordance with the teaching of Example 2A except that BamHI and BglII restriction enzymes and salts, rather than HphI and PstI restriction enzymes and salts, were used.

B. BamHI Digestion of Plasmid pUC7

The desired digestion was done in substantial accordance with the teaching of Example 2A except that 1 μg. of plasmid pUC7 (commercially available from Bethesda Research Laboratories, 8717 Grovemont Circle, P.O. Box 6009, Gaithersburg, Md. 20877), rather than the BamHI linker-containing DNA, was used.

C. Ligation and Transformation

About 1 μg. of the ~1.3 kb BamHI-BglII fragment of plasmid pIT123 was ligated into about 1 μg. of BamHI-digested pUC7 and then the resultant mixture was used to transform *E. coli* K12 RR1ΔM15 (deposited and made part of the permanent stock culture collection of the National Regional Research Laboratory, Peoria, Ill. from which it can be obtained under the accession number NRRL B-15440). Both procedures are carried out in substantial accordance with the ligation and transformation teachings of Example 2B. The transformed cells were plated onto TY plates containing 50 μg./ml. ampicillin, 100 mM isopropylthio-β-D-galactoside (IPTG), and 0.02% 5-bromo-4-chloro-3-indolyl-β-D-galactoside (X-gal). White ampicillin-resistant colonies were plated on TY containing ampicillin (50 μg./ml.), hygromycin B (200 μg./ml.) and IPTG (100 mM). The hygromycin B resistant cells constituted the desired *E. coli* K12 RR1ΔM15/pIT144 transformants, the identity of which was further confirmed by restriction enzyme, and agarose gel electrophoresis analysis of the constitutive plasmids. The resultant *E. coli* K12 RR1ΔM15/pIT144 transformants were then conventionally cultured for subsequent production and isolation of plasmid pIT144. Plasmid pIT144 can transform conventional *E. coli* strains such as, for example, *E. coli* K12, *E. coli* K12 RR1, *E. coli* K12 JA221 and *E. coli* K12 HB101 in substantial accordance with the transformation teaching of Example 2B. A restriction site map of plasmid pIT144 is presented in FIG. 2 of the accompanying drawings.

EXAMPLE 4

Construction of Plasmid pIT208 and *E. coli* K12 JA221/pIT208

A. Construction of Plasmid pIT207

1. Construction and Isolation of the ~750 bp BamHI-BglII Fragment of Plasmid pIT118
   a. Isolation of Plasmid pIT118
   Plasmid pIT118 can be isolated from *E. coli* K12 JA221/pIT118 in substantial accordance with the teaching of Example 1A. The aforementioned strain has been deposited and made part of the permanent stock culture collection of the Northern Regional Research Laboratory, Peoria, Ill., under the accession number NRRL B-15441.
   b. Digestion
   The desired digestion and isolation were carried out in substantial accordance with the teaching of Example 2A except that BamHI and BglII restriction enzymes, rather than HphI and PstI restriction enzymes, were used.

2. BamHI Digestion of Plasmid pMC1587
   The desired digestion was carried out in substantial accordance with the teaching of Example 2A except that 2 μg. of plasmid pMC1587, rather than the BamHI linker-containing DNA, were used. Plasmid pMC1587 can be conventionally isolated, in substantial accordance with the teaching of Example 1A, from *E. coli* K12 JA221/pMC1587, a strain deposited and made part of the permanent stock culture collection of the Northern Regional Research Laboratory, Peoria, Ill., under the accession number NRRL B-15442. Since plasmid pMC1587 has a single BamHI site, digestion is easily monitored by agarose gel electrophoresis. The appearance of a single band of about 16 kb signals complete digestion.

3. Ligation and Transformation of *E. coli* K12 JA221
   About 1 μg. of the ~750 bp BamHI-BglII fragment of plasmid pIT118 was ligated into about 1 μg. of BamHI-digested plasmid pMC1587 and then the resultant ligation mixture was used to transform *E. coli* K12 JA221 (NRRL B-15211). Both procedures were carried out in substantial accordance with the ligation and transformation teachings of Example 2B. The ampicillin resistant transformants were conventionally screened for the presence and correct orientation of the ~750 bp fragment by restriction enzyme and agarose gel electrophoretic analysis of the constitutive plasmids. Plasmids with the BamHI/BglII junction (formed by the ligation of the ~750 bp fragment), oriented closest to the leu 2 gene constituted the desired plasmid pIT207. The *E. coli* K12 JA221/pIT207 transformants were cultured for subsequent production and isolation of plasmid pIT207.

B. Final Construction of Plasmid pIT208

1. BamHI Digestion of Plasmid pIT207
   The desired digestion was carried out in substantial accordance with the teaching of Example 2A except that 1 μg. of plasmid pIT207, rather than the BamHI linker-containing DNA, was used.

2. Ligation and Construction of *E. coli* K12 JA221-/pIT208

About 2 μg. of the ~1.3 kb BamHI-BglII fragment of plasmid pIT123 (prepared in Example 3A) were ligated into about 2 μg. of BamHI-digested plasmid pIT207 and then the resultant ligation mixture was used to transform *E. coli* K12 JA221 (NRRL B-15211). Both procedures were carried out in substantial accordance with the ligation and transformation teachings of Example 2B. The ampicillin resistant transformants were conventionally screened for the presence and correct orientation of the ~1.3 kb fragment by restriction enzyme and agarose gel electrophoretic analysis of the constitutive plasmids. Plasmids with the internal EcoRI site of the ~1.3 kb fragment oriented closest to the leu 2 gene constituted the desired pIT208 plasmids. The *E. coli* K12 JA221/pIT208 transformants were cultured for subsequent production and isolation of plasmid pIT208.

Plasmid pIT208 contains (1) the truncated YG101 gene fused in translational reading to the DNA of the present invention; (2) the yeast leu 2 gene, allowing for selection of the plasmid via complementation of leu 2 auxotrophs; (3) the yeast 2 micron sequences, facilitating autonomous replication in yeast; (4) the origin of replication from plasmid pBR322, facilitating autonumous replication in *E. coli*; and (5) the β-lactamase gene from pBR322, facilitating plasmid selection in *E. coli*. A restriction site map of plasmid pIT208 is presented in FIG. 3 of the accompanying drawings.

EXAMPLE 5

Construction of *Saccharomyces cerevisiae*/pIT208

*Saccharomyces cerevisiae* cells were transformed with plasmid pIT208 in substantial accordance with the teaching of Hinnen et al., 1978, Proc. Nat. Acad. Sci. USA 75:1929. Although any yeast can be used, the particular strain exemplified herein is *Saccharomyces cerevisiae* DBY746. The strain is available to the public from the Yeast Genetics Stock Center, Department of Biophysics and Medical Physics, University of California, Berkeley, Calif. 94720.

The desired construction was made by growing about 100 ml. of yeast cells at 30° C. in YPD medium (1% Bacto-yeast extract, 2% Bacto-peptone, and 2% D-glucose) to an A600 of about 1. Under sterile conditions, the cells were centrifuged and washed twice in 15 ml. of 1.2M sorbitol and then resuspended in 15 ml. of the sorbitol solution. After about 100 μl. of 2.5 mg./ml. zymolyase* (60,000 units in 5 mM KP04, pH 7.6, 1.2M sorbitol) were added, the cells were incubated at 30° C. The extent of protoplasting was monitored by adding 180 μl. of 10% SDS to 20 ml. aliquots and then observing under phase contrast microscopy. When about 90% of the cells appeared black, the cells were harvested by gentle centrifugation, washed twice with 15 ml. of 1.2M sorbitol( resuspended in 10 ml. of 1.2M sorbitol-0.5X YPD solution and incubated at room temperature for 40 minutes. The cells were again collected by gentle centrifugation and resuspended in 600 μl of a solution comprising 0.5X YPD, 1.2M sorbitol, 10 mM CaCl and 10 mM Tris-HCl, pH 7.5. Aliquots (0.2 ml) of these cells were removed and added to 20 μl. of the solution containing the DNA in 1.2M sorbitol. The mixture was incubated at room temperature for 10 minutes, at which time 1 ml. of a solution comprising 20% PEG 4000**, 10 mM CaCl₂, 10 mM Tris-HCl, pH 7.5 was added. The mixture was incubated at room temperature for 60 minutes and then divided into four portions. Each portion was added to tubes containing 25 ml. of 3% agar, 0.67% Difco yeast nitrogen base without amino acids, 1.2M sorbitol, 2% glucose, 2% YPD and other conventional nutrients. In addition, histidine, uracil and tryptophan were also added to select for leucine prototrophy. The cells were gently mixed, immediately added to an empty sterile petri dish and, after the agar solidified, incubated at 30° C. under moist conditions. After about 3 days, leucine prototrophs were picked and streaked on YPD plates containing 500 μg./ml. Hygromycin B. The resultant hygromycin B-resistant yeast cells constituted the desired *Saccharomyces cerevisiae*/pIT208 transformants. The identity of the transformants was further confirmed by restriction enzyme and agarose gel electrophoretic analysis of the constitutive plasmids.

*Zymolyase can be obtained from the following source: Miles Laboratory, P.O. Box 2000, Elkhart, Id. 46515
**PEG 4000 can be obtained from the following source: Baker Biochemicals, 222 Red School Lane, Phillipsburg, N.J. 08865

EXAMPLE 6

Construction of Plasmid pKC307 and *E. coli* K12 RR1ΔM15/pKC307

A. Construction of Plasmid pIT104 and *E. coli* K12 RR1/pIT104

About 1.5 μl. (1 μg.) of SacI-cut plasmid pKC222, 0.5 μl. of 10X buffer (0.5M Tris, pH 7.5, 0.1M MgCl₂), 0.5 μl. each of (200 mM) dCTP, dATP, TTP and dGTP and 1 μl. (containing 1 unit of DNA polymerase I large (Klenow) fragment were incubated at 37° C. for 15 minutes. After heat inactivation of the polymerase, BamHI linkers* were added in substantial accordance with the procedure of Roberts and Lauer, 1979. The resultant BamHI linker-containing DNA was conventionally digested with BamHI restriction enzyme and then ligated in substantial accordance with the procedure of Example 2B. After digestion with SacI restriction enzyme to reduce the number of parental plasmids, the resultant plasmid pIT104 DNA was used to transform, in substantial accordance with the procedure of Wensink, 1974, *E. coli* K12 RR1 (NRRL B-15210). The transformed cells were plated on LB plates (Rosenberg and Court, 1979, Ann. Rev. Genet. 13:319) containing ampicillin at 50 μg./ml. The resultant ampicillin resistant *E. coli* K12 RR1/pIT104 cells were conventionally isolated and cultured for the subsequent production and isolation of plasmid pIT104. The structure of plasmid pIT104 was confirmed by transformation, selection, restriction enzyme and sequence analysis.

*BamHI linkers [d(CCGGATCCGG)] can be obtained from the following source: Collaborative Research, 128 Spring Street, Lexington, Mass. 02173

B. HphI Digestion of Plasmid pIT104

The desired digestion was carried out in substantial accordance with the teaching of Example 2A except that plasmid pIT104, rather than plasmid pKC222, was used and, in addition, there was no subsequent PstI digestion. The resultant plasmid pIT104 HphI digest was used without purification.

C. HincII Digestion of Plasmid pUC8

The desired digestion was carried out in substantial accordance with the teaching of Example 2A except that plasmid pUC8 (commercially available from Bethesda Research Laboratories, 8717 Grovemont Circle, P.O. Box 6009, Gaithersburg, Md. 20877), and HincII restriction enzyme and reaction mix*, rather than plasmid pKC222 and HphI and PstI restriction enzymes and salts, were used. The resultant plasmid pUC8 HincII digest was used without purification.

*Reaction mix for HincII restriction enzyme was prepared with the following preferred composition: 50 mM NaCl, 10 mM Tris-HCl, pH 7.5, 10 mM MgCl$_2$, 1 mM Dithiothreitol

D. Removal of 3' Extensions with T4 DNA Polymerase

The 3' extension left by the HphI digestion of Example 6B was removed for subsequent blunt end ligation. Thus, about 1 μg. of the plasmid pIT104 HphI digest was incubated in 10 μl of a solution comprising 33 mM Tris-HCl, pH 7.8, 67 mM potassium acetate, 10 mM magnesium acetate, 0.5 mM dithiothreitol, 0.1 mg./ml. BSA, 150 μM each of dCTP, dATP, dGTP and TTP and 3 units cf T4 DNA polymerase at 37° C. for about 5 minutes. The reaction was conventionally terminated by incubation at 65° C. after addition of about 1 μl. of 50 mM EDTA.

E. Ligation and Construction of E. coli K12 RR1ΔAM15/pKC307

Figure 4:
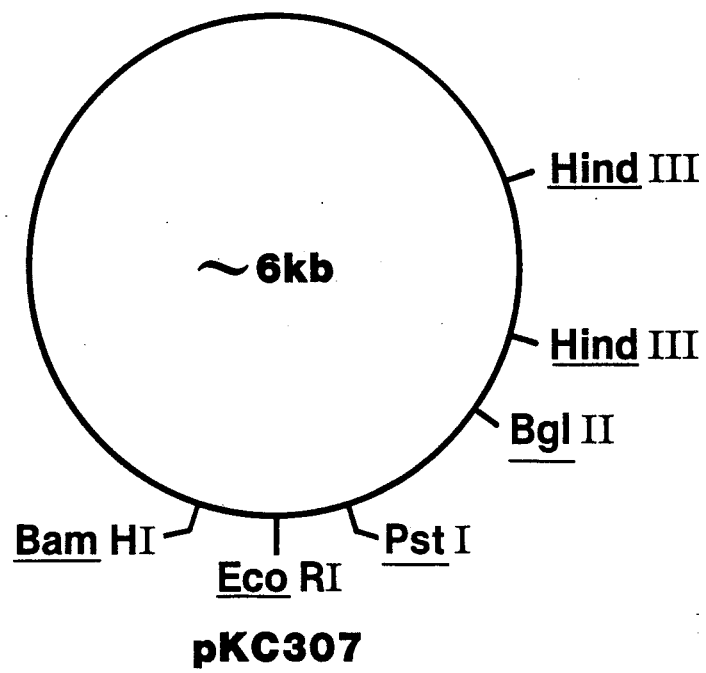
FIG. 4, depicts the restriction site maps of plasmids pKC307 and pIT125.
Figure 4:
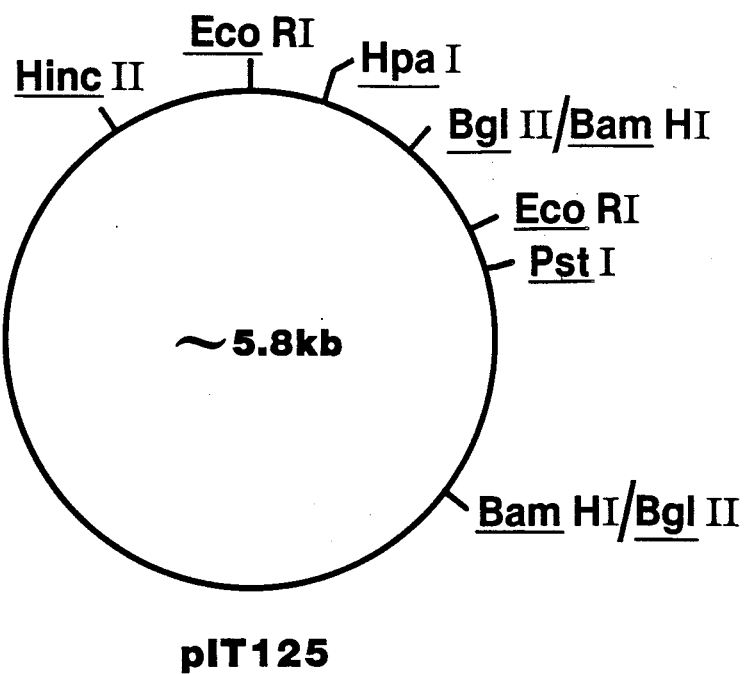

Ligation of the blunt ended plasmid pIT104 and plasmid pUC8 digests was conventionally carried out in substantial accordance with the ligation procedure of Maniatis et al. 1982. The resultant plasmid, designated as pKC307, was used to transform *E. coli* K12 RR1ΔM15 in substantial accordance with the transformation procedure of Example 2B and the selection procedure of Example 3C. The resultant *E. coli* K12 RR1ΔM15/pKC307 transformants were then conventionally cultured for subsequent production and isolation of plasmid pKC307. Plasmid pKC307 can transform conventional *E. coli* strains such as, for example, *E. coli* K12, *E. coli* K12 RR1, *E. coli* K12 JA221 and *E. coli* K12 HB101 in substantial accordance with the transformation teaching of Example 2B. A restriction site map of plasmid pKC307 is presented in FIG. 4 of the accompanying drawings.

A functionally equivalent derivative of plasmid pKC307 was also prepared by conventionally deleting the ~1.7 kb HindIII fragment of the aforementioned plasmid. The resultant plasmid, designated as pKC308, was used to transform *E. coli* K12 JA221 and serves to further exemplify the present invention.

EXAMPLE 7

Construction of Plasmid pIT125 and E. coli K12 JA221/pIT125

1. Construction of Plasmid pIA7Δ4Δ1

A. Construction of Plasmid pBRHtrp

Plasmid pGM1 carries the *E. coli* tryptophan operon containing the deletion ΔLE1413 (Miozzari, et al., 1978, *J. Bacteriology*, 1457–1466) and hence expresses a fusion protein comprising the first 6 amino acids of the trp leader and approximately the last third of the trp E polypeptide (hereinafter referred to in conjunction as LE'), as well as the trp D polypeptide in its entirety, all under the control of the trp promoter-operator system. *E. coli* K12 W3110tna2trp-Δ102/pGM1 has been deposited with the American Type Culture Collection (ATCC No. 31622) and pGM1 may be conventionally removed from the strain for use in the procedures described below.

About 20 μg. of the plasmid were digested with the restriction enzyme PvuII which cleaves the plasmid at five sites. The gene fragments were next combined with EcoRI linkers (consisting of a self complementary oligonucleotide of the sequence: pCATGAATTCATG) providing an EcoRI cleavage site for later cloning into a plasmid containing an EcoRI site. The 20 μg of DNA fragments obtained from pGM1 were treated with 10 units T$_4$ DNA ligase in the presence of 200 pico moles of the 5'-phosphorylated synthetic oligonucleotide pCATGAATTCATG and in 20 μl T$_4$ DNA ligase buffer (20 mM tris, pH 7.6, 0.5 mM ATP, 10 mM MgCl$_2$, 5 mM dithiothreitol) at 4° C. overnight. The solution was then heated 10 minutes at 70° C. to halt ligation. The linkers were cleaved by EcoRI digestion and the fragments, now with EcoRI ends, were separated using 5 percent polyacrylamide gel electrophoresis (herein after "PAGE"). The three largest fragments were isolated from the gel by first staining with ethidium bromide and then locating the fragments with ultraviolet light and cutting from the gel the portions of interest. Each gel fragment, with 300 microliters 0.1xTBE, was placed in a dialysis bag and subjected to electrophoresis at 100 v for one hour in 0.1xTBE buffer (TBE buffer contains: 10.8 g. Tris base, 5.5 g. boric acid, 0.09 g. Na$_2$EDTA in 1 liter H$_2$O). The aqueous solution was collected from the dialysis bag, phenol extracted, chloroform extracted, and made 0.2M with respect to sodium chloride. The DNA was then recovered in water after ethanol precipitation. The trp promoter/operator-containing gene with EcoRI sticky ends was identified in the procedure next described, which entails the insertion of fragments into a tetracycline sensitive plasmid which, upon promoter/operator insertion, becomes tetracycline resistant. All DNA fragment isolations hereinafter described are performed using PAGE followed by the electroelution method described above.

B. Construction of Plasmid pBRH trp Expressing Tetracycline Resistance Under the Control of the Trp Promoter/Operator and Identification and Amplification of the Trp Promoter/Operator Containing DNA Fragment Isolated in 'A' above.

Plasmid pBRH1, (constructed in accordance with Rodriguez, et al., 1979, Nucleic Acids Research 6, 3267–3287 and West et al., 1979, Gene 7:271–288 and also deposited in the American Type Culture Collection under the accession number ATCC 37070) expresses ampicillin resistance and contains the gene for tetracycline resistance but, there being no associated promoter, does not express that resistance. The plasmid is accordingly tetracycline sensitive. By introducing a promoter/operator system in the EcoRI site, the plasmid can be made tetracycline resistant.

Plasmid pBRH1 (ATCC 37070) was digested with EcoRI. The enzyme was removed by phenol extraction followed by chloroform extraction and then the DNA was recovered in water after ethanol precipitation. The resulting DNA molecule was, in separate reaction mixtures, combined with each of the three DNA fragments obtained in Example 7A and ligated with T$_4$ DNA ligase as previously described. The DNA in the reaction mixture was used to transform competent *E. coli* K12 strain 294, (Backman et al., 1976, Proc. Nat. Acad. Sci. U.S.A. 73:4174–4198, ATCC No. 31446) by standard techniques (Hershfield et al., 1974, Proc. Nat. Acad. Sci. U.S.A. 71:3455–3459) and the bacteria were then plated on LB plates containing 20 μg./ml. ampicillin and 5 μg./ml. tetracycline.

Several tetracycline-resistant colonies were selected and the plasmid DNA was isolated and designated pBRHtrp. The presence of the desired fragment was confirmed by restriction enzyme analysis. Plasmid pBRH trp expresses β-lactamase, imparting ampicillin resistance, and contains a DNA fragment which includes the trp promoter/operator. The DNA fragment also codes for a first protein, (designated LE'), comprising a fusion of the first six amino acids of the trp leader and approximately the last third of the trp E polypeptide, a second protein (designated D'), corresponding to approximately the first half of the trp D polypeptide, and a third protein, coded for by the tetracycline resistance gene.

C. Construction of Plasmid pSOM7Δ2

Plasmid pBRHtrp was digested with EcoRI restriction enzyme and the resulting fragment, isolated by PAGE and electroelution, was combined with EcoRI-digested plasmid pSOM11 (Itakura et al., 1977, Sci. 198:1056, G. B. Patent Publication No. 2,007,676A). The mixture was ligated with T4 DNA ligase and the resulting DNA transformed into E. coli K12 strain 294 as previously described. Transformant bacteria were selected on ampicillin-containing plates and the resulting ampicillin-resistant colonies were screened by colony hybridization (Gruenstein et al., 1975, Proc. Nat. Acad. Sci. U.S.A. 72:3951 3965). The trp promoter/operator-containing fragment, isolated from pBRH trp and then radioactively labelled with $^{32}p$, was used as a probe in the above procedure. Several colonies were shown to be positive by colony hybridization and were therefore selected. Plasmid DNA was isolated and the orientation of the inserted fragments was determined by restriction analysis using enzymes BglII and BamHI in double digestion. Colonies containing the desired plasmid with the trp promoter/operator fragment in the proper orientation were grown in LB medium containing 10 μg./ml. ampicillin. The desired plasmid was designated pSOM7Δ2 and was used for subsequent constructions described below.

D. Construction of Plasmid pTrp24

1. Construction of a Gene Fragment Comprising Codons for the Distal Regions of the LE' Polypeptide With BglII and EcoRI Restriction Sites Respectively at the 5' and 3' Ends of the Coding Strand Plasmid pSOM7Δ2 was HindIII digested followed by digestion with lambda exonuclease (a 5' to 3' exonuclease) under conditions chosen so as to digest beyond the BglII restriction site within the LE' encoding region. About 20 μg. of HindIII-digested pSOM7Δ2 was dissolved in buffer (20 mM glycine buffer, pH 9.6, 1 mM MgCl$_2$, 1 mM β-mercaptoethanol). The resulting mixture was treated with 5 units of lambda exonuclease for 60 minutes at room temperature. The reaction mixture obtained was then phenol extracted, chloroform extracted, and ethanol precipitated.

To create an EcoRI residue at the distal end of the LE' gene fragment, a primer $^{32}$pCCTGTGCATGAT was synthesized by the improved phosphotriester method (Crea et al., 1978), and hybridized to the single stranded end of the LE' gene fragment resulting from lambda exonuclease digestion. The hybridization was performed by dissolving 20 μg. of the lambda exonuclease-treated HindIII digestion product of plasmid pSOM7Δ2 in 20 μl. H$_2$O and combining with 6 μl. of a solution containing approximately 80 picomoles of the 5'-phosphorylated oligonucleotide described above. The synthetic fragment was hybridized to the 3' end of the LE' coding sequence and the remaining single strand portion of the LE' fragment was filled in by Klenow Polymerase I using dATP, TTP, dGTP and dCTP. Klenow Polymerase I is the fragment obtained by proteolytic cleavage of DNA Polymerase I. It contains the 5' T 3' polymerizing activity, the 3'→5' exonucleolytic activity, but not the 5'→3' exonucleolytic activity of the parental enzyme (Kornberg, 1974, W. H. Freeman and Co., San Francisco, Calif.).

The reaction mixture was thus heated to 50° C. and let cool slowly to 10° C., whereafter 4 μl. of Klenow enzyme were added. After 15 minutes incubation at room temperature followed by 30 minutes incubation at 37° C., the reaction was stopped by the addition of 5 μl. of 0.25M EDTA. The reaction mixture was phenol extracted, chloroform extracted, and ethanol precipitated. The DNA was subsequently cleaved with the restriction enzyme BglII and the fragments were separated by PAGE. An autoradiogram obtained from the gel revealed a $^{32}$P-labelled fragment, which was recovered by electroelution, of the expected length of approximately 470 bp. As outlined, this fragment LE'(d) has a BglII terminus and a blunt end coinciding with the beginning of the primer.

2. Construction of Plasmid pThα1

Plasmid pThα1 was constructed by inserting a synthesized gene for thymosin alpha 1 into plasmid pBR322. The synthesis of the thymosin alpha 1 coding DNA involves the synthesis and subsequent ligation of the 16 oligonucleotides (T$_1$ through T$_{16}$) that are indicated by the double headed arrows in FIG. 5 of the accompanying drawings. A Met codon ATG was inserted at the N-terminus and the 5' ends were designed with single-stranded cohesive termini to facilitate joining to plasmids cleaved with EcoRl and BamHI. As can be readily appreciated, the BglII site in the center of the gene assists in the analysis of recombinant plasmids.

Oligodeoxyribonucleotides T$_1$ to T$_{16}$ were synthesized by the modified phosphotriester method using fully protected trideoxyribonucleotide building blocks (Itakura et al., 1977 and Crea et al., 1978). The various oligodeoxyribonucleotides are shown below in Table 1.

TABLE 1

| | SYNTHETIC OLIGONUCLEOTIDES FOR THYMOSINαl GENE | | |
|---|---|---|---|
| Compound | Sequence | Length | HPLC Analysis Retention Time (min)* |
| T$_1$ | A-A-T-T-C-A-T-G-T-C | 10 | 17.4 |
| T$_2$ | T-G-A-T-G-C-T-G-C-T-G-T-T-G-A | 15 | 24.3 |
| T$_3$ | T-A-C-T-T-C-T-T0C-T-G-A | 12 | 20.3 |
| T$_4$ | G-A-T-T-A-C-T-A-C-T-A-A-A | 13 | 22.0 |
| T$_5$ | G-C-A-G-C-A-T-C-A-G-A-C-A-T-G | 15 | 24.8 |
| T$_6$ | G-A-A-G-T-A-T-C-A-A-C-A | 12 | 20.1 |
| T$_7$ | A-G-T-A-A-T-C-T-C-A-G-A-A | 13 | 22.6 |
| T$_8$ | A-A-G-A-T-C-T-T-T-A-G-T | 12 | 20.2 |
| T$_9$ | G-A-T-C-T-T-A-A-G-G-A-G | 12 | 20.4 |
| T$_{10}$ | A-A-G-A-A-G-G-A-A-G-T-T | 12 | 21.1 |
| T$_{11}$ | G-T-C-G-A-A-A-G-A-G-G-C-T | 13 | 20.5 |
| T$_{12}$ | G-A-G-A-A-C-T-A-A-T-A-G | 12 | 20.4 |
| T$_{13}$ | C-T-T-C-T-T-C-T-C-C-T-T | 12 | 19.9 |
| T$_{14}$ | T-T-C-G-A-C-A-A-C-T-T-C | 12 | 20.5 |
| T$_{15}$ | G-T-T-C-T-C-A-G-C-C-T-C | 12 | 20.2 |
| T$_{16}$ | G-A-T-C-C-T-A-T-T-A | 10 | 17.2 |

*at ambient temperature

Figure 6:
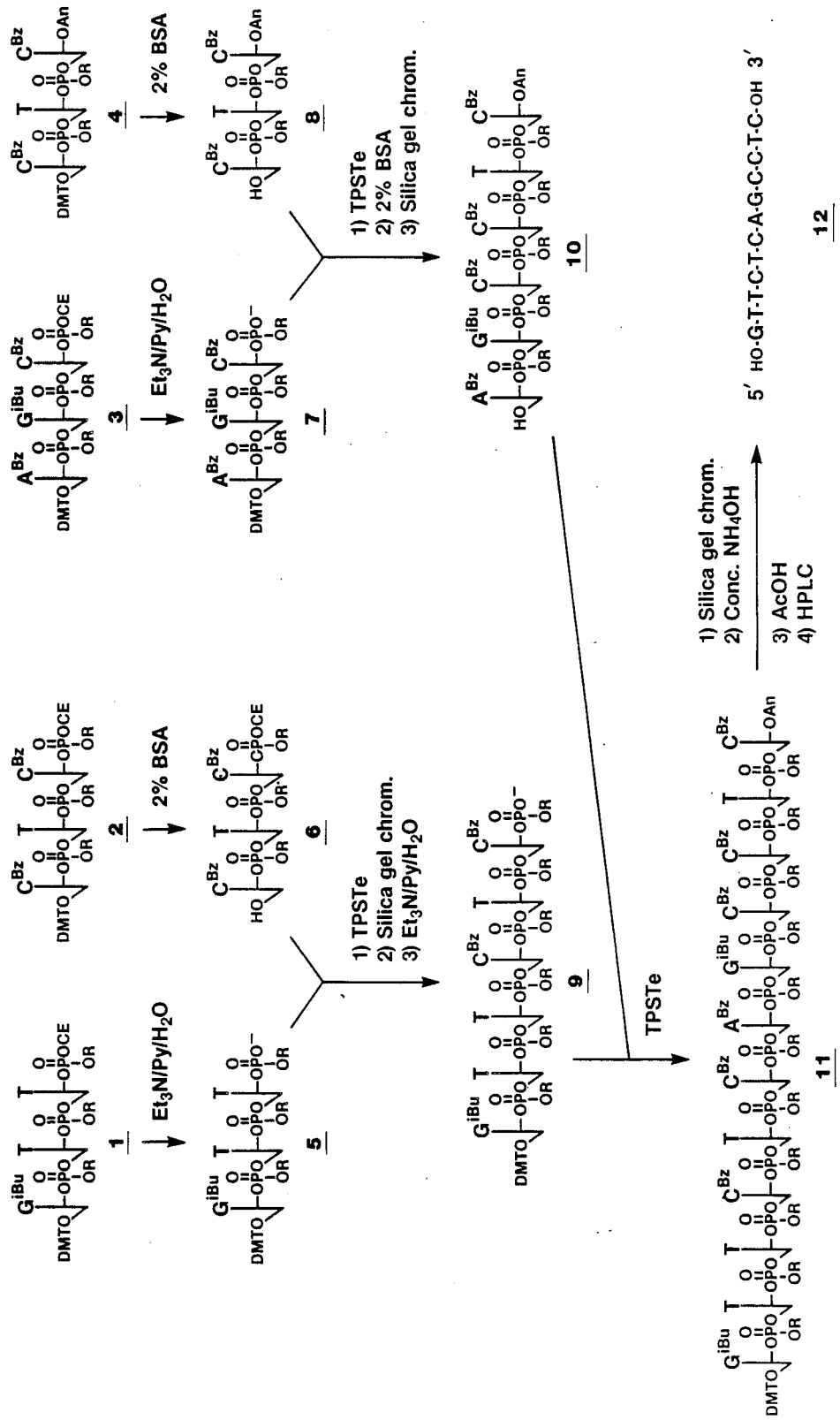
FIG. 6, depicts the synthesis procedure for fragment $T_{15}$.

The above synthesis is typified by the following procedure for fragment $T_{15}$ as summarized in FIG. 6 of the accompanying drawings. Various nucleotide fragments that are used in the synthesis of $T_{15}$ are numerically designated in the figure. The abbreviations employed are as follows: TPSTe, 2,4,6-triisopropylbenzenesulfonyltetrazole; BSA, benzene sulfonic acid; TLC, thin layer chromatography; HPLC, high performance liquid chromatography; DMT, 4,4'-dimethoxytrityl; CE, 2-cyanoethyl; R, p-chlorophenyl; Bz, benzoyl; An, anisoyl; iBu, isobutryl; Py, pyridine; AcOH, acetic acid; $Et_3N$, triethylamine.

The fully protected trideoxyribonucleotides 4 (85 mg., 0.05 mM) and 2 (180 mg., 0.1 mM) were deblocked at the 5' hydroxyls by treatment with 2% BSA in 7:3 (v/v) chloroform/methanol (10 and 20 ml., respectively) for 10 minutes at 0° C. Reactions were stopped by addition of saturated aqueous ammonium bicarbonate (2 ml.), extracted with chloroform (25 ml.) and washed with water (2×10 ml.). The organic layers were dried (magnesium sulfate), concentrated to small volumes (about 5 ml.) and precipitated by addition of petroleum ether (35°-60° C. fraction). The colorless precipitates were collected by centrifugation and dried in a desiccator in vacuo to give 6 and 8 respectively, each homogeneous by silica gel tlc (Merck 60 F254, chloroform/methanol, 9:1).

Trimers 1 and 3 (270 mg., 0.15 mM; 145 mg., 0.075 mM) were converted into their phosphodiesters (5 and 7) by treatment with triethylamine/pyridine/water (1:3:1, v/v, 10 ml.) for 25 minutes at ambient temperature. Reagents were removed by rotary evaporation and the residues dried by repeated evaporations with anhydrous pyridine (3×10 ml.). Trimer 8 (0.05 mM) and trimer 7 were combined with TPSTe (50 mg., 0.15 mM) in anhydrous pyridine (3 ml.) and the reaction mixture left in vacuo at ambient temperature for two hours. TLC analysis showed that 95% of the trimer 8 had been converted into hexamer product (visualized by detection of the DMT group by spraying with 10% aqueous sulfuric acid and heating at 60° C.). The reaction was quenched by addition of water (0.1 ml.) and the solvent evaporated under reduced pressure. After removal of pyridine by coevaporations with toluene, the hexamer was deblocked at the 5' position with 2% BSA (8 ml.) as described above for trimers 4 and 2. The product (10) was purified on a silica gel column (Merck 60 H, 3.5×5 cm.) by step gradient elution with chloroform/methanol (98:2 to 95:5, v/v). Fractions containing product 10 were evaporated to dryness.

Similarly, trimer 5 was coupled to 6 and the fully protected product directly purified on silica gel. This latter compound was deblocked at the 3' end by triethylamine/pyridine/water as described above to give fragment 9.

Finally, hexamers 9 and 10 were coupled in anhydrous pyridine (2 ml.) with TPSTe (75 mg., 0.225 mM) as the condensing agent. Upon completion (4 hours, ambient temperature) the mixture was rotary evaporated and the residue chromatographed on silica gel. Product 11 (160 mg.) was obtained by precipitation with petroleum ether and appeared homogeneous on TLC. A portion of compound 11 (20 mg.) in pyridine (0.5 ml.) was completely deblocked by treatment with concentrated ammonium hydroxide (7 ml., 8 hours, 60° C.) and subsequent treatment in 80% acetic acid (15 minutes, ambient temperature). After evaporation of acetic acid, the solid residue was dissolved in 4% aqueous ammonium hydroxide (v/v, 4 ml.) and extracted with ethyl ether (3×2 ml.). The aqueous phase was concentrated to 1-2 ml. and a portion applied to HPLC for purification of 12. The fractions corresponding to the major peak were pooled (ca. 2.0 $O.D._{254}$ units) and concentrated to about 5 ml. The final product 12 was desalted on Bio-gel P-2 (1.5×100 cm.) by elution with 20% aqueous ethanol, reduced to dryness and resuspended in water (200 μl.) to give a solution of $A_{254}=10$. The sequence of 12 was confirmed by two-dimensional sequence analysis.

Figure 7:
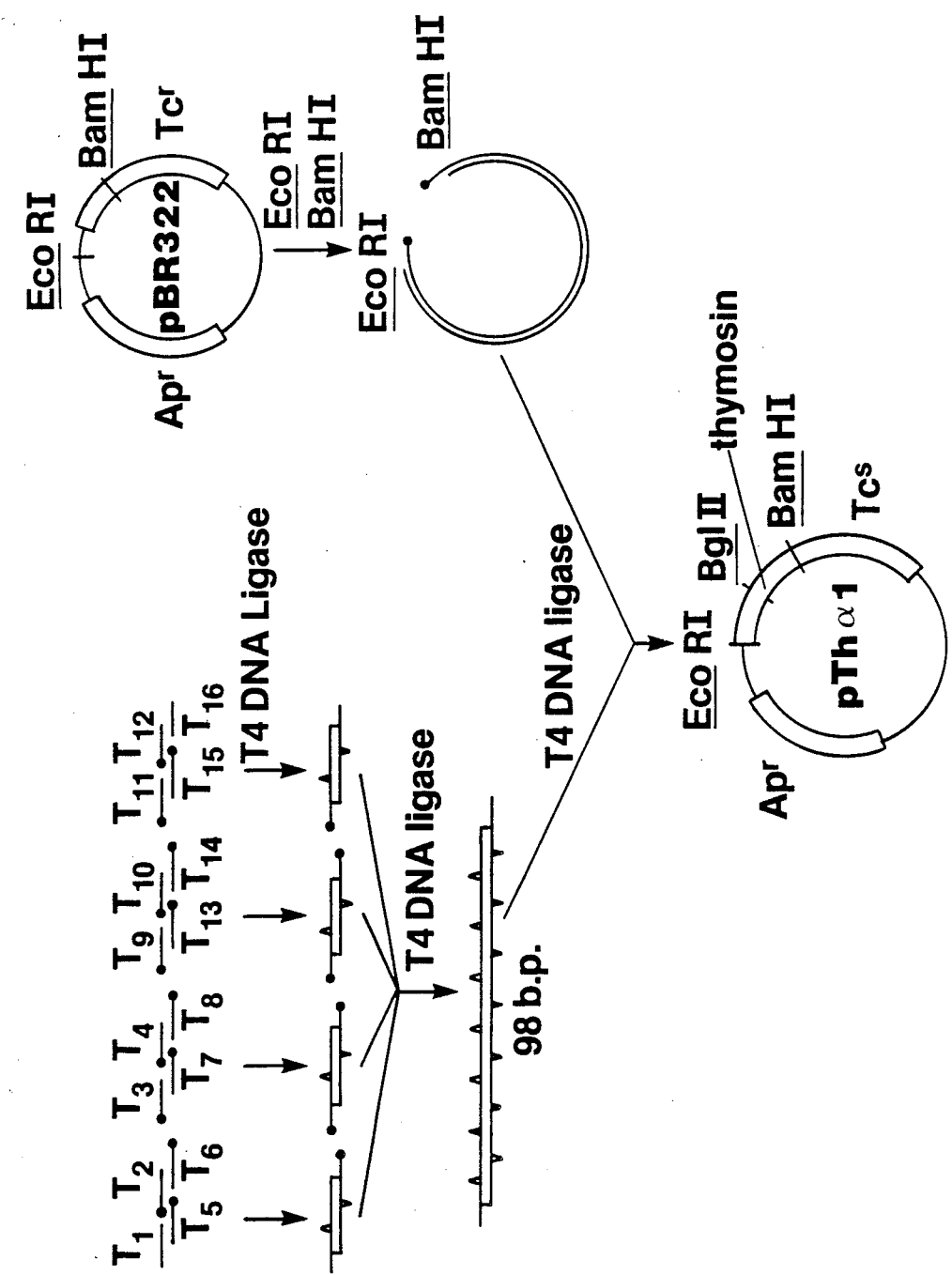
FIG. 7, depicts the construction route for plasmid pTh alpha 1.

The complete thymosin alpha 1 gene was assembled from the 16 synthetic oligo-nucleotides by methods previously described in detail for somatostatin (Itakura et al., 1977) and growth hormone (Goeddel et al., 1979, Nature 281:544). Ten microgram quantities of oligonucleotides $T_2$ through $T_{15}$ were quantitatively phosphorylated with [γ-$^{32}$P]-ATP (New England Nuclear) in the presence of $T_4$ polynucleotide kinase (Goeddel et al, 1979), to give specific activities of approximately 1 Ci/mmol. Radiolabelled fragments were purified by 20% polyacrylamide/7M urea gel electrophoresis and sequences of the eluted fragments were verified by two-dimensional electrophoresis/homochromatography (Jay et al., 1974, Nucleic Acids Res. 1:331) of partial snake venom digests. Fragments $T_1$ and $T_{16}$ were left unphosphorylated to minimize undesired polymerization during subsequent ligation reactions. These oligonucleotides (2 μg. each) were assembled in four groups of four fragments (See FIG. 7 of the accompanying drawings), by $T_4$ DNA ligase using published procedures (Goeddel et al., 1979). The reaction products were purified by gel electrophoresis on a 15% polyacrylamide gel containing 7M urea (Maxam and Gilbert, 1977, Proc. Nat. Acad. Sci. U.S.A. 71:3455). The four isolated products were ligated together and the reaction mixture resolved by 10% polyacrylamide gel electrophoresis. DNA in the size range of the thymosin alpha 1 gene (90–105 base pairs) was electroeluted.

Figure 5:
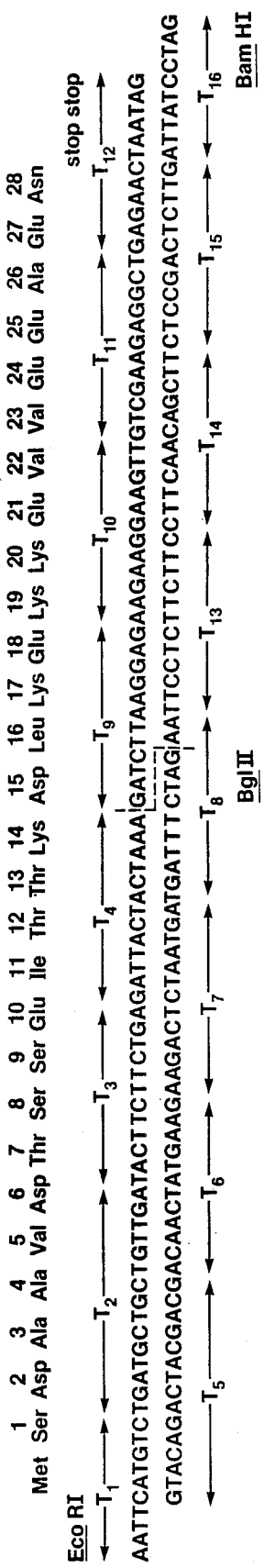
FIG. 5, depicts the tymosin alpha I gene.

Plasmid pBR322 (0.5 μg.) was treated with BamHI and EcoRI restriction endonucleases and the fragments separated by polyacrylamide gel electrophoresis. The large fragment was recovered from the gel by electroelution and subsequently ligated to the assembled synthetic DNA (Goeddel et al., 1979). This mixture was used to transform *E. coli* K12 strain 294, ATCC No. 31446. Five percent of the transformation mixture was plated on LB plates containing 20 μg./ml. ampicillin. The ampicillin resistant colonies obtained were sensitive to tetracycline, suggesting insertion into the tetracycline resistance gene. Analysis of the plasmids from these colonies showed that in each case the plasmid, designated pThα1, contained (a) a BglII site not found in pBR322 itself, thus indicating the presence of the thymosin alpha 1 gene as shown in FIG. 5, and (b) a fragment of approximately 105 base pairs generated by BamHI/EcoRI cleavage. The construction route for plasmid pThα1 (not drawn to scale), is presented in FIG. 7 of the accompanying drawings wherein the heavy dots indicate 5'-phosphate groups.

3. Reaction of Treated pThα1 and LE'(d) Fragment

The plasmid pThα1 contains a gene specifying ampicillin resistance and a structural gene specifying thymosin alpha 1 cloned at its 5' coding strand end into an EcoRI site and at its 3' end into a BamHI site. The thymosin gene contains a BglII site as well. To create a plasmid capable of accepting the LE'(d) fragment prepared above, pThα1 was EcoRI digested followed by Klenow polymerase I reaction with TTP and dATP to blunt the EcoRI residues. BglII digestion of the resulting product created a linear DNA fragment containing the gene for ampicillin resistance and, at its opposite ends, a sticky BglII residue and a blunt end. The resulting product could be recircularized by reaction with the LE'(d) fragment containing a BglII sticky end and a blunt end in the presence of T4 ligase to form the plasmid pTrp24. In doing so, an EcoRI site is recreated at the position where blunt end ligation occurred.

E. Construction of Plasmid pSOM7Δ2Δ4

Successive digestion of pTrp24 with BglII and EcoRI, followed by PAGE and electroelution, yields a fragment having codons for the LE'(d) polypeptide with a BglII sticky end and an EcoRI sticky end adjacent to its 3' coding terminus. The LE'(d) fragment can be cloned into the BglII site of plasmid pSom7Δ2 to form an LE' polypeptide/somatostatin fusion protein expressed under the control of the tryptophan promoter/operator. To do so requires (1) partial EcoRI digestion of pSom7Δ2 in order to cleave the EcoRI site distal to the tryptophan promoter/operator, and (2) proper choice of the primer sequence to properly maintain the codon reading frame and recreate an EcoRI cleavage site.

Thus, 16 μg. of plasmid pSom7Δ2 was diluted into 200 μl. of buffer containing 20 mM Tris, pH 7.5, 5 mM MgCl$_2$, 0.02 NP40 detergent, and 100 mM NaCl and treated with 0.5 units EcoRI. After 15 minutes at 37° C., the reaction mixture was phenol extracted, chloroform extracted, ethanol precipitated, and subsequently digested with BglII. The larger resulting fragment was isolated by the PAGE procedure followed by electroelution. This fragment contains the codons "LE'(p)" for the proximal end of the LE' polypeptide, i.e., those upstream from the BglII site. This fragment was next ligated to the above LE'(d) fragment in the presence of T4 DNA ligase to form the plasmid pSom7Δ2Δ4, which upon transformation into *E. coli* strain 294, efficiently produced a fusion protein consisting of the fully reconstituted LE polypeptide and somatostatin under the control of the tryptophan promoter/operator.

F. Construction of Linear DNA Having a PstI Residue at the 3' end and a BglII Residue at its 5' End Bounding a Gene Specifying Tetracycline Resistance Plasmid pBR322 was HindIII digested and the protruding HindIII ends were digested with S1 nuclease. The S1 nuclease digestion involved treatment of 10 μg. of HindIII-cleaved pBR322 in 30 μl. S1 buffer (0.3M NaCl, 1 mM MnCl$_2$, 25 mM sodium acetate, pH 4.5) with 300 units S1 nuclease for 30 minutes at 15° C. The reaction was stopped by the addition of 1 μl. of 30 X S1 nuclease stop solution (0.8M tris base, 50 mM EDTA). The mixture was phenol extracted, chloroform extracted, ethanol precipitated, and then EcoRI digested as previously described. The resulting fragment, obtained by the PAGE procedure followed by electroelution, has an EcoRI sticky end and a blunt end whose coding strand begins with the nucleotide thymidine. The S1-digested HindIII residue beginning with thymidine can be joined to a Klenow Polymerase I-treated BglII residue so as to reconstitute the BglII restriction site upon ligation.

Therefore plasmid pSOM7Δ2, prepared in Example 7-1C, was BglII digested and the resulting BglII sticky ends were made double stranded by treatment with Klenow Polymerase I using all four deoxynucleotide triphosphates. EcoRI cleavage of the resulting product, followed by PAGE and electroelution of the small fragment, yielded a linear piece of DNA containing the tryptophan promoter/operator and codons of the LE' "proximal" sequence upstream from the BglII site ("LE'(p)"). The product had an EcoRI end and a blunt end resulting from filling in the BglII site. However, the BglII site is reconstituted by ligation of the blunt end to the blunt end of the above S1-digested HindIII fragment. Thus, the two fragments were ligated in the presence of T4 DNA ligase to form the recircularized plasmid pHKY10 which was propagated by transformation into competent *E. coli* strain 294 cells. Tetracycline resistant cells bearing the recombinant plasmid pHKY10 were selected and the plasmid DNA extracted. Digestion with BglII and PstI, followed by isolation by the PAGE procedure and electroelution of the large fragment, yielded the desired linear piece of DNA having PstI and BglII sticky ends. This DNA fragment, thus produced from pHKY10, contains the origin of replication and therefore is useful as a component in the construction of plasmid pIA7Δ4Δ1 in which both the genes coding for the trp LE' polypeptide fusion protein and the tetracycline resistance are controlled by the trp promoter/operator.

G. Construction of Linear DNA Having the Trp Promoter/Operator

Plasmid pSOM7Δ2Δ4, prepared in Example 7-1C, was subjected to partial EcoRI digestion followed by PstI digestion. The resulting fragment contained the trp promoter/operator and was isolated by the PAGE procedure followed by electroelution. Partial EcoRI digestion was necessary to obtain a fragment which was cleaved adjacent to the 5' end of the somatostatin gene but not cleaved at the EcoRI site present between the ampicillin resistance gene and the trp promoter/operator. Ampicillin resistance lost by the PstI cut in the ampicillin resistance gene can be restored upon ligation with the final pHKY10 linear DNA derivative produced in Example 7-1F above.

H. Isolation of the Insulin A Chain Structural Gene

The insulin A chain structural gene was obtained by the EcoRI and BamHI digestion of plasmid pIA1, whose construction is disclosed in Goeddel et al., 1979, Proc. Nat. Acad. Sci. U.S.A. 76:106. The plasmid can also be obtained from *E. coli* K12 strain 94/pIA1 (ATCC 31448). The desired fragment was purified by PAGE and electroelution and had EcoRI and BamHI termini.

Figure 8:
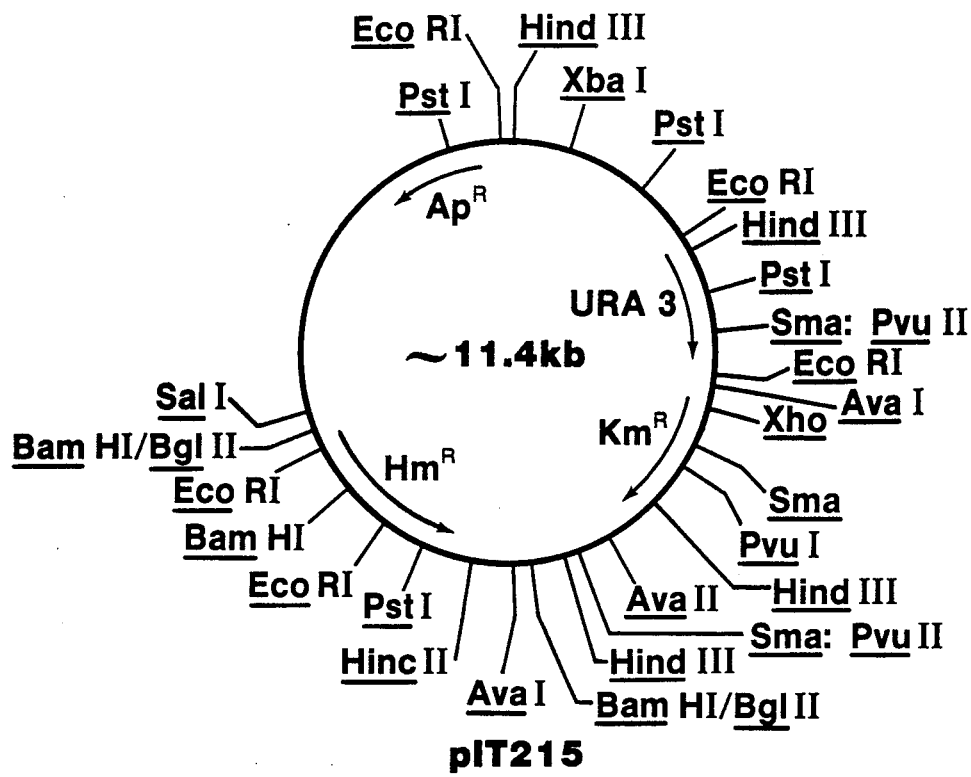
FIG. 8, depicts the restriction site maps for plasmids pIT215 and pIT217.
Figure 8:
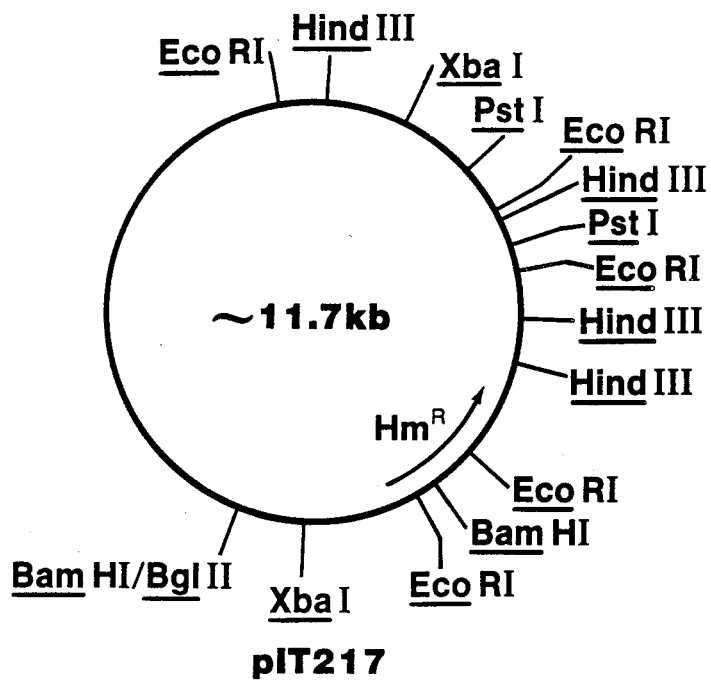

I. Ligation of the Insulin A Chain Structural Gene, the Trp Promoter/Operator and the pHKY10 Linear DNA Fragment Having PstI and BglII Termini The Insulin A Chain structural gene, the linear DNA fragment containing the trp promoter/operator (prepared in Example 7-1G), and the pHKY10 linear DNA fragment (prepared in Example 7-1F), were ligated together in proper orientation, as depicted in FIG. 8, to form the desired plasmid pIA7Δ4Δ1. Plasmid pIA7Δ4Δ1 can be readily selected because of the restoration of ampicillin and tetracycline resistance.

2. Ligation of the Plasmid pIT123 ~1.3 kb BamHI-BglII and Plasmid pIA7Δ4Δ1 ~4.5 kb BamHI-BglII Fragments

A. BamHI-BglII Digestion of Plasmid pIA7Δ4Δ1 and Isolation of the ~4.5 kb Fragment The desired digestion and isolation were carried out in substantial accordance with the teaching of Example 2A except that plasmid pIA7Δ4Δ1 and BglII and BamHI restriction enzymes and manufacturer-recommended salts, rather than plasmid pIT123 and HphI and PstI restriction enzymes and salts, were used.

B. Ligation and Transformation

The desired ligation and transformation was carried out in substantial accordance with the teaching of Example 3C except that the ~4.5 kb BamHI-BglII fragment of plasmid pIA7Δ4Δ1 and *E. coli* K12 JA221 (NRRL B-15211), rather than plasmid pUC7 and *E. coli* K12 RR1ΔM15, were used. The transformed cells were plated onto TY plates containing 50 μg./ml. ampicillin and subsequently patched onto plates containing 200 μg./ml. hygromycin B. The desired hygromycin B resistant *E. coli* K12 JA221/pIT125 transformants were conventionally cultured for subsequent production and isolation of plasmid pIT125. Plasmid pIT125 can transform conventional *E. coli* strains such as, for example, *E. coli* K12, *E. coli* K12 RR1 and *E. coli* K12 HB101 in substantial accordance with the transformation teaching of Example 2B. A restriction site map of plasmid pIT125 is presented in FIG. 4 of the accompanying drawings.

Additional illustrative plasmids and transformants constructed in accordance with the foregoing teachings are presented below in Tables 2 and 3.

*E. coli* K12 RR1/R
*Saccharomyces cerevisiae*/R$^1$
wherein R is selected from the group consisting of plasmids pIT143, pIT212, pIT213, pIT215, pIT217 and pIT219 and wherein R$^1$ is selected from the group consisting of plasmids pIT212, pIT213, pIT215, pIT217 and pIT219.

We claim:

1. A DNA sequence which encodes the amino acid sequence

R$_2$ PRO GLU LEU THR ALA THR SER VAL GLU LYS PHE
LEU ILE GLU LYS PHE ASP SER VAL SER ASP LEU
MET GLN LEU SER GLU GLY GLU GLU SER ARG ALA
PHE SER PHE ASP VAL GLY GLY ARG GLY TYR VAL
LEU ARG VAL ASN SER CYS ALA ASP GLY PHE TYR
LYS ASP ARG TYR VAL TYR ARG HIS PHE ALA SER
ALA ALA LEU PRO ILE PRO GLU VAL LEU ASP ILE
GLY GLU PHE SER GLU SER LEU THR TYR CYS ILE
SER ARG ARG ALA GLN GLY VAL THR LEU GLN ASP
LEU PRO GLU THR GLU LEU PRO ALA VAL LEU GLN
PRO VAL ALA GLU ALA MET ASP ALA ILE ALA ALA
ALA ASP LEU SER GLN THR SER GLY PHE GLY PRO
PHE GLY PRO GLN GLY ILE GLY GLN TYR THR THR
TRP ARG ASP PHE ILE CYS ALA ILE ALA ASP PRO HIS
VAL TYR HIS TRP GLN THR VAL MET ASP ASP THR
VAL SER ALA SER VAL ALA GLN ALA LEU ASP GLU
LEU MET LEU TRP ALA GLU ASP CYS PRO GLU VAL
ARG HIS LEU VAL HIS ALA ASP PHE GLY SER ASN
ASN VAL LEU THR ASP ASN GLY ARG ILE THR ALA
VAL ILE ASP TRP SER GLU ALA MET PHE GLY ASP
SER GLN TYR GLU VAL ALA ASN ILE PHE PHE TRP
ARG PRO TRP LEU ALA CYS MET GLU GLN GLN THR
ARG TYR PHE GLU ARG ARG HIS PRO GLU LEU ALA
GLY SER PRO ARG LEU ARG ALA TYR MET LEU ARG
ILE GLY LEU ASP GLN LEU TYR GLN SER LEU VAL
ASP GLY ASN PHE ASP ASP ALA ALA TRP ALA GLN

TABLE 2

Figure 9:
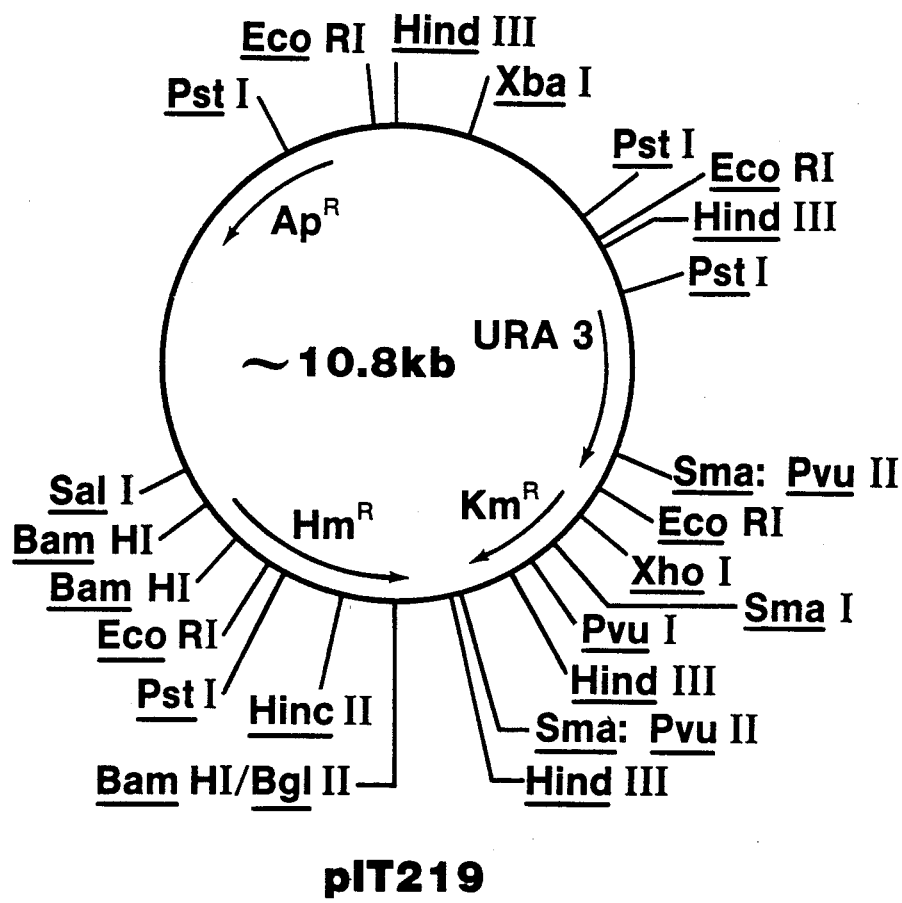
FIG. 9, depicts the restriction site map for plasmid pIT219.

| | | | Represenative Plasmids | | |
|---|---|---|---|---|---|
| Example No. | Name | ~ Size (in kb) | Markers | | Construction |
| | | | *E. coli* | Yeast | |
| 8 | pIT143 | 3.0 | Ap$^R$ | | MboII digestion of the ~958 bp ClaI-HincII fragment of pIT141 followed by removal of the extensions, attachment of BamHI linkers of the sequence TGGATCCA and ligation into BamHI-digested plasmid pUC8 |
| 9 | pIT212 | 8.9 | Ap$^R$ | URA3 | Ligation of ~1.3 kb BamHI-BglII fragment of pIT123 into BamHI-digested pRB5 (ATCC No. 37051) |
| 10 | pIT213 | 10.6 | Ap$^R$ Km$^R$ | URA3 | Ligation of ~1.7 kb PvuII fragment of plasmid pNG59* into SmaI-digested plasmid pIT212 |
| 11 | pIT215 | 11.4 | Ap$^R$ Km$^R$ | URA3 Hm$^R$ | Ligation of ~750 bp BamHI-BglII fragment of pIT118 into BamHI-digested plasmid pIT213 in the orientation depicted in FIG. 8. |
| 12 | pIT217 | 11.7 | Ap$^R$ Km$^R$ | URA3 Hm$^R$ | Ligation of ~1 kb BamHI-BglII fragment of pIT120 into BamHI-digested plasmid pIT213 in the orientation depicted in FIG. 8. |
| 13 | pIT219 | 10.8 | Ap$^r$ Km$^R$ | URA3 Hm$^R$ | Ligation of the ~230 bp BamHI fragment of plasmid pIT143 into BamHI-digested plasmid pIT213 in the orientation depicted in FIG. 9. |

*Plasmid pNG59 can be obtained and conventionally isolated from *E. coli* K12 RR1/pNG59, a strain deposited and made part of the permanent stock culture collection of the Northern Regional Research Laboratory, Peoria, Illinois. The strain is available as a preferred source and stock reservoir of the plasmid under the accession number NRRL B-15604.

TABLE 3

Representative Transformants

*E. coli*/R
*E. coli* K12/R
*E. coli* K12 JA221/R
*E. coli* K12 HB101/R

GLY ARG CYS ASP ALA ILE VAL ARG SER GLY ALA
GLY THR VAL GLY ARG THR GLN ILE ALA ARG ARG
SER ALA ALA VAL TRP THR ASP GLY CYS VAL GLU
VAL LEU ALA ASP SER GLY ASN ARG ARG PRO SER
THR ARG PRO ARG ALA LYS GLU wherein
MET is methionine, LYS is lysine,
PRO is proline,
GLU is glutamic acid,
LEU is leucine,
THR is threonine,
ALA is alamine,
SER is serine,
VAL is valine,
PHE is phenylalanine,
ILE is isoleucine,
GLY is glycine,
ASP is aspartic acid, GLN is glutamine,
ARG is arginine,
CYS is cysteine,
TRP is tryptophan,
ASN is asparagine,
HIS is histidine,
TYR is tyrosine, and
R is a deoxyribonucleotide triplet that encodes lysine and z=0 to 2; subject to the limitation that said DNA encodes a hygromycin B phosphotransferase that is not encoded by plasmid pKC203.

2. The DNA of claim 1, wherein the DNA comprises

```
Rm  R²n         CCT GAA CTC   ACC GCG ACG   TCT GTC GAG AAG
 |    |         ||| ||| |||   ||| ||| |||   ||| ||| ||| |||
R¹m R³n         GGA CTT GAG   TGG CGC TGC   AGA CAG CTC TTC

TTT CTG ATC   GAA AAG TTC   GAC AGC GTC   TCC GAC CTG ATG
||| ||| |||   ||| ||| |||   ||| ||| |||   ||| ||| ||| |||
AAA GAC TAG   CTT TTC AAG   CTG TCG CAG   AGG CTG GAC TAC

CAG CTC TCG   GAG GGC GAA   GAA TCT CGT   GCT TTC AGC TTC
||| ||| |||   ||| ||| |||   ||| ||| |||   ||| ||| ||| |||
GTC GAG AGC   CTC CCG CTT   CTT AGA GCA   CGA AAG TCG AAG

GAT GTA GGA   GGG CGT GGA   TAT GTC CTG   CGG GTA AAT AGC
||| ||| |||   ||| ||| |||   ||| ||| |||   ||| ||| ||| |||
CTA CAT CCT   CCC GCA CCT   ATA CAG GAC   GCC CAT TTA TCG

TGC GCC GAT   GGT TTC TAC   AAA GAT CGT   TAT GTT TAT CGG
||| ||| |||   ||| ||| |||   ||| ||| |||   ||| ||| ||| |||
ACG CGG CTA   CCA AAG ATG   TTT CTA GCA   ATA CAA ATA GCC

CAC TTT GCA   TCG GCC GCG   CTC CCG ATT   CCG GAA GTG CTT
||| ||| |||   ||| ||| |||   ||| ||| |||   ||| ||| ||| |||
GTG AAA CGT   AGC CGG CGC   GAG GGC TAA   GGC CTT CAC GAA

GAC ATT GGG   GAA TTC AGC   GAG AGC CTG   ACC TAT TGC ATC
||| ||| |||   ||| ||| |||   ||| ||| |||   ||| ||| ||| |||
CTG TAA CCC   CTT AAG TCG   CTC TCG GAC   TGG ATA ACG TAG

TCC CGC CGT   GCA CAG GGT   GTC ACG TTG   CAA GAC CTG CCT
||| ||| |||   ||| ||| |||   ||| ||| |||   ||| ||| ||| |||
AGG GCG GCA   CGT GTC CCA   CAG TGC AAC   GTT CTG GAC GGA

GAA ACC GAA   CTG CCC GCT   GTT CTG CAG   CCG GTC GCG GAG
||| ||| |||   ||| ||| |||   ||| ||| |||   ||| ||| ||| |||
CTT TGG CTT   GAC GGG CGA   CAA GAC GTC   GGC CAG CGC CTC

GCC ATG GAT   GCG ATC GCT   GCG GCC GAT   CTT AGC CAG ACG
||| ||| |||   ||| ||| |||   ||| ||| |||   ||| ||| ||| |||
CGG TAC CTA   CGC TAG CGA   CGC CGG CTA   GAA TCG GTC TGC

AGC GGG TTC   GGC CCA TTC   GGA CCG CAA   GGA ATC GGT CAA
||| ||| |||   ||| ||| |||   ||| ||| |||   ||| ||| ||| |||
TCG CCC AAG   CCG GGT AAG   CCT GGC GTT   CCT TAG CCA GTT

TAC ACT ACA   TGG CGT GAT   TTC ATA TGC   GCG ATT GCT GAT
||| ||| |||   ||| ||| |||   ||| ||| |||   ||| ||| ||| |||
ATG TGA TGT   ACC GCA CTA   AAG TAT ACG   CGC TAA CGA CTA

CCC CAT GTG   TAT CAC TGG   CAA ACT GTG   ATG GAC GAC ACC
||| ||| |||   ||| ||| |||   ||| ||| |||   ||| ||| ||| |||
GGG GTA CAC   ATA GTG ACC   GTT TGA CAC   TAC CTG CTG TGG
```

```
GTC AGT GCG     TCC GTC GCG     CAG GCT CTC     GAT GAG CTG ATG
||| ||| |||     ||| ||| |||     ||| ||| |||     ||| ||| ||| |||
CAG TCA CGC     AGG CAG CGC     GTC CGA GAG     CTA CTC GAC TAC

CTT TGG GCC     GAG GAC TGC     CCC GAA GTC     CGG CAC CTC GTG
||| ||| |||     ||| ||| |||     ||| ||| |||     ||| ||| ||| |||
GAA ACC CGG     CTC CTG ACG     GGG CTT CAG     GCC GTG GAG CAC

CAC GCG GAT     TTC GGC TCC     AAC AAT GTC     CTG ACG GAC
||| ||| |||     ||| ||| |||     ||| ||| |||     ||| ||| |||
GTG CGC CTA     AAG CCG AGG     TTG TTA CAG     GAC TGC CTG

AAT GGC CGC     ATA ACA GCG     GTC ATT GAC     TGG AGC GAG GCG
||| ||| |||     ||| ||| |||     ||| ||| |||     ||| ||| ||| |||
TTA CCG GCG     TAT TGT CGC     CAG TAA CTG     ACC TCG CTC CGC

ATG TTC GGG     GAT TCC CAA     TAC GAG GTC     GCC AAC ATC TTC
||| ||| |||     ||| ||| |||     ||| ||| |||     ||| ||| ||| |||
TAC AAG CCC     CTA AGG GTT     ATG CTC CAG     CGG TTG TAG AAG

TTC TGG AGG     CCG TGG TTG     GCT TGT ATG     GAG CAG CAG ACG
||| ||| |||     ||| ||| |||     ||| ||| |||     ||| ||| ||| |||
AAG ACC TCC     GGC ACC AAC     CGA ACA TAC     CTC GTC GTC TGC

CGC TAC TTC     GAG CGG AGG     CAT CCG GAG     CTT GCA GGA TCG
||| ||| |||     ||| ||| |||     ||| ||| |||     ||| ||| ||| |||
GCG ATG AAG     CTC GCC TCC     GTA GGC CTC     GAA CGT CCT AGC

CCG CGG CTC     CGG GCG TAT     ATG CTC CGC     ATT GGT CTT GAC
||| ||| |||     ||| ||| |||     ||| ||| |||     ||| ||| ||| |||
GGC GCC GAG     GCC CGC ATA     TAC GAG GCG     TAA CCA GAA CTG

CAA CTC TAT     CAG AGC TTG     GTT GAC GGC     AAT TTC GAT GAT
||| ||| |||     ||| ||| |||     ||| ||| |||     ||| ||| ||| |||
GTT GAG ATA     GTC TCG AAC     CAA CTG CCG     TTA AAG CTA CTA

GCA GCT TGG     GCG CAG GGT     CGA TGC GAC     GCA ATC GTC CGA
||| ||| |||     ||| ||| |||     ||| ||| |||     ||| ||| ||| |||
CGT CGA ACC     CGC GTC CCA     GCT ACG CTG     CGT TAG CAG GCT

TCC GGA GCC     GGG ACT GTC     GGG CGT ACA     CAA ATC GCC CGC
||| ||| |||     ||| ||| |||     ||| ||| |||     ||| ||| ||| |||
AGG CCT CGG     CCC TGA CAG     CCC GCA TGT     GTT TAG CGG GCG

AGA AGC GCG     GCC GTC TGG     ACC GAT GGC     TGT GTA GAA GTA
||| ||| |||     ||| ||| |||     ||| ||| |||     ||| ||| ||| |||
TCT TCG CGC     CGG CAG ACC     TGG CTA CCG     ACA CAT CTT CAT

CTC GCC GAT     AGT GGA AAC     CGA CGC CCC     AGC ACT CGT CCG
||| ||| |||     ||| ||| |||     ||| ||| |||     ||| ||| ||| |||
GAG CGG CTA     TCA CCT TTG     GCT GCG GGG     TCG TGA GCA GGC

AGG GCA AAG     GAA R⁴
||| ||| |||     ||| |
TCC CGT TTC     CTT R⁵
``` wherein

A is deoxyadenyl,
G is deoxyguanidyl,
C is deoxycytidyl and
T is thymidyl

R and $R^2$ are deoxyribonucleotide triplets that independently encode lysine, $R^1$ and $R^3$ are deoxyribonucleotide triplets wherein the nitrogenous bases are complementary to the respective and corresponding bases of R and $R^2$, m and n=0 or 1, subject to the limitation that when n=0, then m=0 and when m=1, then n=1, $R^4$ is a deoxyribonucleotide triplet that encodes a translational stop codon and $R^5$ is a deoxyribonucleotide triplet wherein the nitrogenous bases are complementary to the corresponding bases of $R^4$.

3. The DNA of claim 2 wherein n=1 and m=0.
4. The DNA of claim 2 wherein m and n=1.
5. The DNA of claim 2 wherein m and n=0.
6. The DNA of claim 2 which is in translational reading phase with a transcriptional and translational activator sequence.

7. The DNA of claim 6 that further comprises up to the first 15 amino-terminal codons of a structural gene homologous to the transcriptional and translational activator sequence.

8. The DNA of claim 6 wherein m and n=0, $R^4$ is TAG and $R^5$ is ATC.

9. The DNA of claim 8 wherein the gene homologous to the transcriptional and translational activator sequence is a bacterial gene.

10. The DNA of claim 9 wherein the gene encodes up to 15 amino acids.

11. The DNA of claim 10 wherein the gene is a portion of the E. coli lac Z gene.

12. The DNA of claim 8 wherein the gene is a eukaryotic gene.

13. The DNA of claim 12 wherein the gene is a portion of the yeast heat shock gene.

14. A recombinant DNA cloning vector comprising the DNA of claim 1.

15. The recombinant DNA cloning vector of claim 14 which is a plasmid.

16. A recombinant DNA cloning vector comprising the DNA of claim 2.

17. The recombinant DNA cloning vector of claim 16 which is a plasmid.

18. A plasmid comprising the DNA of claim 7.

19. A plasmid comprising the DNA of claim 9.

20. A plasmid comprising the DNA of claim 10.

21. A plasmid comprising the DNA of claim 11.

22. A plasmid comprising the DNA of claim 12.

23. A plasmid comprising the DNA of claim 13.

24. The plasmid of claim 17 which is plasmid pIT123.

25. The plasmid of claim 18 which is plasmid pIT144.

26. The plasmid of claim 18 which is plasmid pKC307.

27. The plasmid of claim 18 which is plasmid pKC308.

28. The plasmid of claim 18 which is plasmid pIT125.

29. The plasmid of claim 23 which is plasmid pIT208.

30. The plasmid pIT207.

31. A transformant comprising the DNA of claim 1.

32. A transformant comprising the DNA of claim 2.

33. A transformant comprising the plasmid of claim 18.

34. A transformant comprising the plasmid of claim 19.

35. A transformant comprising the plasmid of claim 22.

36. A transformant comprising the plasmid of claim 23.

37. The transformant of claim 34 which is E. coli.

38. The transformant of claim 32 which is E. coli K12 JA221/pIT123.

39. The transformant of claim 37 which is E. coli K12 JA221/pIT144.

40. The transformant of claim 32 which is E. coli K12/pIT208.

41. The transformant of claim 32 which is E. coli K12 JA221/pKC307.

42. The transformant of claim 32 which is E. coli K12 JA221/pIT125.

43. The transformant of claim 32 which is E. coli K12 JA221/pIT208.

44. The transformant of claim 32 which is Saccharomyces cerevisiae/pIT208.

45. The DNA of claim 2 which is the ~1.3 kb BamHI-BglII restriction fragment of plasmid pIT123.

46. A plasmid selected from the group consisting of plasmids pIT141, pIT143, pIT212, pIT213, pIT215, pIT217 and pIT219.

47. The plasmid of claim 46 which is pIT141.

48. The plasmid of claim 46 which is pIT143.

49. The plasmid of claim 46 which is pIT215.

50. The plasmid of claim 46 which is pIT217.

51. The plasmid of claim 46 which is pIT219.

52. A transformed E. coli host cell which comprises a plasmid of claim 47.

53. A transformed Saccharomyces cerevisiae host cell which comprises plasmid pIT215 of claim 49.

54. A transformed Saccharomyces cerevisiae host cell which comprises plasmid pIT217 of claim 50.

55. A transformed Saccharomyces cerevisiae host cell which comprises plasmid pIT219 of claim 51.

56. The DNA of claim 1 which is in translational reading phase with a transcriptional and translational activator gene sequence.

* * * * *